United States Patent [19]

Buchardt et al.

[11] Patent Number: 5,580,751
[45] Date of Patent: Dec. 3, 1996

[54] PROCESS FOR THE PREPARATION OF C-TERMINALLY AMIDATED PEPTIDES

[75] Inventors: Ole Buchardt, Værløse; Klaus Breddam, Glostrup, both of Denmark; Dennis Henriksen, Lincoln, Nebr.

[73] Assignee: Carlsberg A/S, Copenhagen, Denmark; a part interest

[21] Appl. No.: 431,539

[22] Filed: Apr. 21, 1995

Related U.S. Application Data

[63] Continuation of Ser. No. 39,306, Apr. 15, 1993, abandoned.

[30] Foreign Application Priority Data

Sep. 14, 1990 [DK] Denmark .................................. 2208/90

[51] Int. Cl.[6] .............................. C12P 21/06; C12N 9/48; C12N 9/76
[52] U.S. Cl. ......................... 435/68.1; 435/212; 435/213
[58] Field of Search ................................... 435/68.1, 212, 435/213

[56] References Cited

U.S. PATENT DOCUMENTS

| | | | |
|---|---|---|---|
| 4,018,790 | 4/1977 | Paget et al. | 548/307.7 |
| 4,062,746 | 12/1977 | Rich et al. | 204/157.68 |
| 4,511,505 | 4/1985 | Morihara et al. | 530/303 |
| 4,708,934 | 11/1987 | Gilligan et al. | 435/68.1 |
| 4,709,014 | 11/1987 | Tamaoki | 530/333 |
| 4,806,473 | 2/1989 | Johansen et al. | 435/68.1 |
| 4,806,534 | 2/1989 | Leonardi et al. | 514/233.5 |
| 4,921,797 | 5/1990 | Matsuo et al. | 435/129 |
| 5,190,875 | 3/1993 | Steinke et al. | 435/227 |

FOREIGN PATENT DOCUMENTS

| | | |
|---|---|---|
| 0017485 | 10/1980 | European Pat. Off. . |
| 0045187 | 2/1982 | European Pat. Off. . |
| 0308067A2 | 3/1989 | European Pat. Off. . |

OTHER PUBLICATIONS

Rich et al., "Removal of C–Terminal peptide Amides from a 3–Nitro–4–Aminomethyl–Benzyl Amide Resin by Photolysis," *Tetrahedron Lett.*, 5:301–304 (1975).

S. Wang, "Solid Phase Synthesis of Protected Peptides via Photolytic Cleavage of the α–Methylphenacyl Ester Anchoring Linkage," *J. Org. Chem.*, 41:3258–3261 (1976).

F. Widmer et al., "Influence of the Structure of Amine Components on Carboxypeptidase Y Catalyzed Amide Bond Formation," *Carlsberg Res. Commun.*, 46:97–106 (1981).

K. Breddam, "Enzymatic Properties of Malt Carboxypeptidase II in Hydrolysis and Aminolysis Reactions" *Carlsberg Res. Commun.*, 50:309–323 (1985).

K. Breddam et al., "Primary Structure and Enzymatic Properties of Carboxypeptidase II from Wheat Bran," *Carlsberg Res. Commun.*, 52:297–311 (1987).

K. Breddam, "Carboxypeptidases S–1 from Penicillium Janthinellum: Enzymatic Properties in Hydrolysis and Aminolysis Reactions," *Carlsberg Res. Commun.*, 53:309–320 (1988).

J. Johansen et al., "Isolation of Carboxypeptidase Y by Affinity Chromatography," *Carlsberg Res. Commun.*, 41:1–14 (1976).

Y. Kubota et al., "Carboxypeptidase $C_n$," *J. Biochem.*, 74:757–770 (1973).

B. Penke et al., "Solid–Phase Synthesis of Peptide Amides on a Polystyrene Support Using Fluorenylmethoxycarbonyl Protecting Groups," *J. Org. Chem*, 52:1197–1200 (1987).

V. Pillai et al., "3 Nitro–4–Aminomethyl Benzoyl Derivatives of Poly Ethylene Glycols: a New Class of Photosensitive Soluble Polymer Carriers for the Synthesis of Carboxy Terminal Peptide Amides," *Tetrahedron Lett.*, 36:3409–3412 (1979). English Abstract—*Chem. Abstracts* 93:740 (1908), Abst. No. 26764X.

V. Pillai et al., "New Easily Removable Poly(ethylene glycol) Supports for the Liquid–Phase Method of Peptide Synthesis," *J. Org. Chem.*, 45:5364–5370 (1980).

A. Ajayaghosh et al., "Solid–Phase Synthesis of N–methyl—and N–Ethylamides of Peptides Using Photolytically Detachable ((3–nitro–4–((alkylamino)methyl) benzamido)methyl)–polystyrene Resin," *J. Org. Chem.*, 55:2826–2829 (1990).

(List continued on next page.)

*Primary Examiner*—David M. Naff
*Assistant Examiner*—Jon P. Weber
*Attorney, Agent, or Firm*—Merchant & Gould, Smith, Edell, Welter & Schmidt, P.A.

[57] ABSTRACT

A process for preparing C-terminally amidated peptides, Peptide-$NH_2$, is presented. In a first step, a substrate component is reacted with a nucleophile component in the presence of trypsin or a carboxypeptidase using as nucleophile a compound $NH_2$—R to form a first reaction product Peptide-NH—R. In a second step, the first reaction product is non-enzymatically chemically cleaved to form the C-terminally amidated product, Peptide-$NH_2$. The substrate component is selected from a) peptide derivatives Peptide-X-Y, where X is an amino acid or peptide residue and Y is OH, OMe or C-terminal modification and c) C-terminally esterified peptides, Peptide-OR', where R' is alkyl, aryl, heteroaryl, or aralkyl. The nucleophile component is selected from

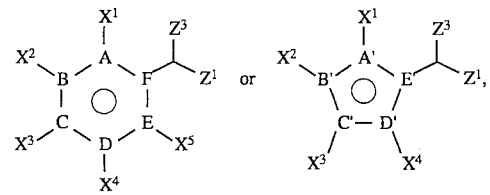

wherein A-F and A'-E' are carbon atoms or up to two hetero atoms, Y is H, alkyl, aryl, aralkyl, oxo or carboxy, $X^1$–$X^5$ are H or various substituents. The cleavage may be induced by photolysis, solvolysis, reduction, rearrangement elimination, or oxidation. The process may be adapted to enzymatic synthesis and lends itself to C-terminal amidation of many types of peptides.

27 Claims, No Drawings

OTHER PUBLICATIONS

K. Breddam et al., "Carboxypeptidase Y Catalyzed Transpeptidations and Enzymatic Peptide Synthesis," *Carlsberg Res. Commun.*, 45:237–247 (1980).

K. Breddam et al., "Carboxypeptidase Y Catalyzed C–Terminal Modifications of Peptides," *Carlsberg Res. Commun.*, 46:121–128 (1981).

K. Breddam et al., "Carboxypeptidase Y Catalyzed C–Terminal Modification in the B–Cahin of Procine Insulin," *Carlsberg Res. Commun.*, 46:361–372 (1981).

K. Breddam et al., "Isolation of Carboxypeptidase from Malted Barley by Affinity Chromatography," *Carlsberg Res. Commun.*, 48:217–230 (1983).

K. Breddham et al., "Carboxypeptidase Y Catalyzed Transpeptidation and Condensation Reactions," *Carlsberg Res. Commun.*, 49:457–462 (1984).

K. Breddam et al., "Malt Carboxypeptidase Catalyzed Aminolysis Reactions", *Carlsberg Res. Commun.*, 49:473–481 (1984).

K. Breddam, "Isolation of Carboxypeptidase II from Malted Barley by Affinity Chromatography," *Carlsberg Res. Commun.*, 50:199–209 (1985).

Breddam, "Serine Carboxypeptidases. A Review", *Carlsberg. Res. Commun.*, 51, 83–128 (1986).

5,580,751

PROCESS FOR THE PREPARATION OF C-TERMINALLY AMIDATED PEPTIDES

This is a continuation of application Ser. No. 08/039,306, filed Apr. 15, 1993, now abandoned.

The present invention relates to a process for the preparation of C-terminally amidated peptides P-$NH_2$, wherein P is a peptide residue which may be N-protected.

The use of biologically active peptides for pharmaceutical purposes and in agriculture has increased the importance of being able to synthesize such compounds in bulk-scale. In principle, three methods are available: (a) chemical synthesis based on solid-phase or solution-phase techniques, (b) enzymatic synthesis, and (c) fermentation with genetically manipulated microorganisms. While the methods (a) and (b), or a combination of them, are the preferred for short peptides they are not suitable for bulk-scale production, they are rather expensive and the yields are often low. It therefore becomes more and more apparent that long peptides in the future will be produced through exploitation of the advances in the methods dealing with recombinant DNA. However, these methods do not permit a number of modifications such as incorporation of D-amino acids or C-terminal amide groups, etc., which may be of importance for the biological activity. A subsequent enzymatic modification is therefore highly desirable and such reactions have been studied to a limited extent.

An enzyme has been described which catalyses the hydroxylation of C-terminal glycyl residues which subsequently decomposes leaving the penultimate residue amidated (U.S. Pat. No. 4,708,934, EP 308067A, DK Application No. 4489/88). This glycine oxidase enzyme which is dependent on $Cu^{2+}$, $O_2$ and ascorbate as cofactors is considered to be the enzyme responsible for in vivo formation of peptide amides. It has been utilised for amidation of peptides in small scale but as it exhibits low activity its applicability for large scale work is still questionable. The enzyme, as isolated from natural sources like rat medullary thyroid carcinoma, is very costly.

Amidation may also by achieved by protease-catalysed condensation reactions (reversal of hydrolysis) using an amino acid amide or peptide amide as nucleophile. The yields of condensation reactions are generally low even in the presence of organic solvents unless the product precipitates in the reaction mixture and this is often not the case with long peptides. In addition, the precursor peptide may exhibit poor solubility in such media. However, serine or thiol-protease catalysed transpeptidation reactions may be carried out in high yield but it is a prerequisite that the enzyme exhibits specificity for a peptide bond close to the C-terminus. Endopeptidases are not generally suitable since they usually will cleave at other positions in the peptide chain as well. Serine carboxypeptidases, on the other hand, exhibit strict specificity for the C-terminal peptide bond and are able to catalyse the exchange of the C-terminal amino acid with an amino acid amide, added to the reaction medium to compete with water as nucleophile.

This property of serine carboxypeptidases was realized by a group of researchers at Carlsberg Research Center and lead to a family of patents based on DK application No. 1443/79 represented by EP Patent No. 17485, U.S. Pat. No. 4,806,534 and its parent U.S. Pat. No. 4,339,534 and WO 80/02151, which lead to i.a. DK Patent No. 155613. These patents were based on the, at that time, surprising finding that exopeptidases were suitable as catalysts for enzymatic peptide synthesis, while the prior art dealt exclusively with endopeptidases. Dependent on the nature of the reactants (substrate and nucleophile components), and the reaction conditions, particularly the pH, serine and thiol carboxypeptidases may catalyze peptide synthesis by chain elongation or by transpeptidation. The preferred enzyme is carboxypeptidase Y (CPD-Y) from yeast. This enzyme reacts with the substrate component under formation of an acyl enzyme intermediate from which the acyl group is transferred to the nucleophile during a transacylation which according to the reaction conditions may be a transpeptidation in which the C-terminal amino acid is exchanged.

The underlying and subsequent research has been further described in a number of articles (Refs. 14–18), which together with the above-mentioned patents are all incorporated by reference.

The general principle of enzymatic peptide synthesis by transpeptidation in the presence of serine or thiol carboxypeptidases is disclosed in U.S. Pat. No. 4,806,473 and its parallel Danish Patent No. 155613. With particular reference to the production of peptide amides these patents generally disclose and claim the production of peptide amides A-B-$NH_2$ where A represent an N-terminal protected amino acid residue or a peptide residue which may be N-terminal protected, and B represents an L-amino acid residue, by reacting as substrate component an optionally N-terminal protected peptide A-X-OH, where A is as defined above and X represents an amino acid residue, with a nucleophile (amine) component H-B-$NH_2$ in the presence of an L-specific serine or thiol carboxypeptidase enzyme from yeast, or of animal, vegetable or microbial origin in an aqueous solution or dispersion of a pH from 5 to 10.5. As further explained in Ref. 14 the preferred pH is about neutral if the formation of a peptide amide is desired.

As a representative example from U.S. Pat. No. 4,806,473 may be mentioned the reaction of Bz-Phe-Gly with Leu-$NH_2$ in the presence of CPD-Y at pH 7.6 and 25° C. leading to the formation of Bz-Phe-Leu-$NH_2$ in a 90% yield. Further examples are incorporated in DK Patent No. 155613 e.g. the reaction of Ac(Ala)$_4$ (SEQ ID NO:1) with Leu-$NH_2$ in the presence of CPD-Y leading to Ac(Ala)$_3$-Leu-$NH_2$ (SEQ ID NO:2) in a yield of 70%.

Similarly, the general principle of enzymatic peptide synthesis by chain elongation is disclosed in U.S. Pat. No. 4,339,534 and the above-mentioned DK patent no. 155,613. With particular reference to the production of peptide amides these patents generally disclose and claim the production of peptide amides A-B-$NH_2$, where A and B are as defined above by reacting a substrate component selected from amino acid and peptide esters, depsipeptides, optionally N-substituted amino acid amides or peptide amides of the formulae A-$OR^1$ or A-$NR^2R^3$, wherein $R^1$ represent alkyl, aryl, heteroaryl, aralkyl or an α-desamino fragment of an amino acid residue, and $R^2$ and $R^3$ are independently selected from H, alkyl, aryl, heteroaryl and aralkyl with a nucleophile (amine) component H-B-$NH_2$.

The preferred reaction mechanism may be termed "aminolysis of esters" i.e. a peptide ester or amino acid ester is used as the substrate component. This reaction is exemplified for a great number of amino acid amide nucleophiles in the above patents. The use of $NH_3$ as nucleophile in the aminolysis under peptide amide formation is shown e.g. in Ref. 15.

Further experiments are disclosed in Ref. 14–18 which support the pioneer character of these early patents and the general applicability of serine carboxypetidases as catalysts for C-terminal modification of peptides.

In order to provide a better understanding of the present invention which is described in more detail below a general discussion of the transpeptidation principle and the competing reactions is deemed proper.

C-terminal amidation of a peptide by means of a serine carboxypeptidase catalysed transpeptidation reaction is dependent on: a) solubility of the peptide in a medium in which the enzyme is active and relatively stable, b) accessibility of the C-terminus to enzymatic cleavage and c) availability of a serine carboxypeptidase of suitable substrate preference.

The types of reactions which may take place are outlined in Scheme 1 with the substrate R-NH-A-B-C-OH and the nucleophile $H-D-NH_2$. The enzyme attacks the C-terminal peptide bond producing an acyl-enzyme intermediate which subsequently may be deacylated by the nucleophile, producing an amidated transpeptidation product (T1), in competition with water, producing a hydrolysis product (H1). The ratio of T1 to H1 may be increased by increasing the concentration of the reactive, deprotonated form of the nucleophile, i.e. by increasing either pH or the added amount of nucleophile. The nature of the leaving group, H-C-OH, has, in the case of CPD-Y, been shown to significantly influence this ratio as well (14, 15) albeit with no obvious trend. Since this amino acid residue does not constitute part of the desired amidated product (T1) it may in principle be chosen freely.

A serine carboxypeptidase may also catalyse the formation of an elongated condensation product (C1) in competition with H1 and T1. However, at the optimal pH-values for transpeptidation such reactions are energically unfavourable in aqueous solution and consequently, at equilibrium, the amount of C1 which may be formed is limited to a few per cent, even at nucleophile concentrations exceeding 1M. Furthermore, the rates of such reactions are normally very low compared to the competing attack on the C-terminal peptide bond, and thus, condensation products are rarely a problem. However, this relation may be reversed in cases where the C-terminal sequence of the peptide does not match the substrate preference of the enzyme with the consequence that small amounts of condensation products are formed in the initial phases of the reaction and then, with time, disappears as the substrate is consumed (16).

The hydrolysis product (HI) may be transformed via the same type of reactions into the products T2, H2 and T1, followed by similar reactions with H2, etc. However, new products may also arise when the enzyme acts on the C-terminal amide bond of T1, i.e. ammonia functions as leaving group, producing another transpeptidation product (TT1) or hydrolysis product (HT1). For these products to appear in significant amounts it is required that the amidase activity towards T1 is significant compared to the peptidase activity towards the substrate and this is normally only the case at pH>9 where the peptidase activity is low and the amidase activity is high or in cases where the peptidase activity is low due to lack of preference for the C-terminal peptide bond.

It is apparent that the action of a serine carboxypeptidase on the C-terminus of a peptide in the presence of an amino acid amide may lead to numerous products of which only T1 is the desired.

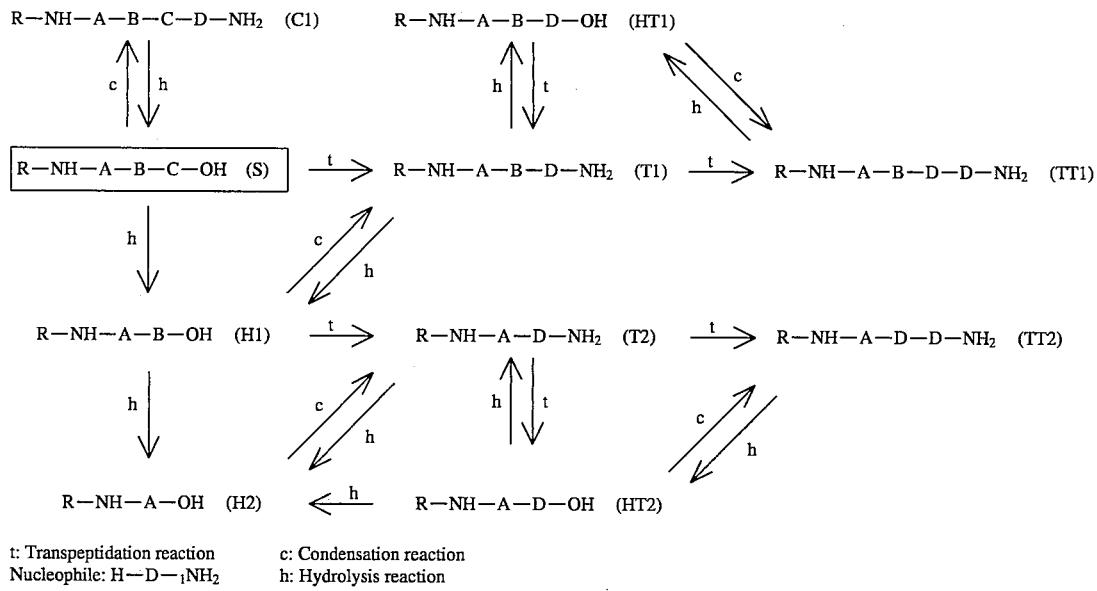

t: Transpeptidation reaction
Nucleophile: $H-D-_1NH_2$
c: Condensation reaction
h: Hydrolysis reaction While reactions with N-blocked dipeptides of a suitable composition relative to the substrate preference of the enzyme in some case lead to yields of T1 approaching 100% (14, 15, 17, 18) the situation is different with larger molecules.

Thus in the patent family represented by EP patent no. 45189, U.S. Pat. No. 4,645,740 and Danish patent no. 148714 incorporated herein by reference a process is described for enzymatic replacement of the B-30 amino acid in insulins, in particular conversion of porcine insulin into human insulin by replacement of the B-30 amino acid alanine with threonine using a serine carboxypeptidase, preferably carboxypeptidase Y from yeast (CPD-Y) or carboxypeptidase P from Penicillium janthinellum (CPD-P) as catalyst and threonine or preferably its amides or esters as the nucleophile component.

While the reaction is only illustrated with unsubstituted threonine amide, the use of N-substituted amino acid amides H-B-NR$^1$R$^2$ is claimed, wherein B is an amino acid and either of R$^1$ and R$^2$ are independently selected from hydrogen, amino, hydroxy, alkyl, cycloalkyl, aryl, heteroaryl or NR$^1$R$^2$ is a heterocyclic group which may contain a further hetero atom.

Thus, depending on the reaction conditions during the transpeptidation step, an optionally N-substituted insulin amide Ins-B-NR$^1$R$^2$ may be formed. This intermediate may be isolated, and, if desired, subsequently deamidated, preferably by enzymatic cleavage, to form the desired free insulin Ins-B-OH or this deamidation may take place in situ by cleavage with the same enzyme as was used during the transpeptidation, preferably CPD-Y.

When porcine insulin was reacted with threonine amide in the presence of CPD-Y at pH 7.5 a complicated mixture of reaction products was obtained (Example 4 of the patents). The mixture was analysed by ion exchange chromatography and three peaks were detected. The peaks were further analyzed by enzymatic digestion and amino acid analysis leading to the following composition (Ins-Pro-Lys-Ala-OH being used to denominate the porcine insulin starting material), and the symbols from Scheme I are used as illustration.

Peak 1: 21% of which
    65% Ins-Pro-Lys-Thr-Thr-NH$_2$ (SEQ ID NO: 3) (TT1)
    35% Ins-Pro-Lys-Thr-NH$_2$ (SEQ ID NO: 6) (T1)
Peak 2: 61% of which
    52% Ins-Pro-Lys-Ala-OH (SEQ ID NO: 6)
    (unreacted porcine insulin) (S)
    26% Ins-Pro-Lys-Thr-OH (SEQ ID NO: 5)
    (human insulin) (HT1)
    22% Ins-Pro-Thr-NH$_2$ (SEQ ID NO: 7) (T2)
Peak 3: 18%
    Breakdown products Thus in the known process only 21% of a mixture of T1 and TT1 was obtained.

The predominant fraction consisted of a mixture of unreacted S, HT1 and T2.

Also a significant amount of breakdown products was obtained.

In example 2 of EP 45187 which was carried out at pH 9.5 80% of the porcine insulin was reacted with threonine amide under formation of what appeared to be human insulin amide (T1) which, however, was further hydrolyzed in situ to human insulin (HT1). A significant amount (20%) had reacted to form H2.

The above-mentioned insulin modification is further analyzed in Refs. 23 and 16.

While therefore the formation of human insulin amide by means of the general principle of transpeptidation described above (S →T1) is certainly possible, it is not easily monitored. Evidently reaction conditions may be selected which on the face of it seem favourable to the formation of T1, but such attempts have not been reported.

Also the separation of the various reactants may be more or less difficult. As T1 lacks the negative charge at the C-terminus it may easily be separated from H1 in preparative scale by ion exchange chromatography. However, provided that the side-chain of the C-terminal amino acid residue is uncharged, T2, T3 etc. as well as C1 and TT1 exhibit the same charge and therefore cannot be separated from T1 by ion exchange chromatography. In such cases preparative HPLC with reverse-phase columns appears to be the only, and a much less attractive, alternative. It is thus more desirable to attempt to suppress the formation of such products by selecting the optimal pH, concentration of nucleophile and most important, the serine carboxypeptidase of the most suitable substrate preference which rapidly and in the highest possible yield converts the substrate in T1 and produces the lowest possible yield, if any, of the undesirable side-products.

To recapitulate the essence of the above observations, incorporation of C-terminal amide groups in peptides by transpeptidation in the presence of a serine carboxypeptidase using the proper amino acid amide as the nucleophile as broadly described and claimed in U.S. Pat. No. 4,806,473 and the other family members is a very appropriate method virtually applicable for any peptide.

However, the process is not always sufficiently selective and necessitates purification procedures in order to remove products of various side reactions in particular when longer peptides are used, in which case the optimal reaction conditions for suppressing the side reactions are difficult to establish.

In Ref. 23 some of the experiments underlying EP patent no. 45187 and its family members were discussed. Here porcine insulin Ins-Pro-Lys-Ala was reacted with i.a. Thr-NH$_2$ and it was concluded that Ins-Pro-Lys-OH was a better substrate that Ins-Pro-Lys-Ala-OH, since Ins-Pro-Thr-NH$_2$ was formed in higher yields than Ins-Pro-Lys-Thr-NH$_2$. By inference Lys in this reaction was a better leaving group than Ala.

Also a significant oligomerization under formation of Ins-Pro-Lys-Thr-Thr-NH$_2$ (SEQ ID NO:3) occurred.

These results were further confirmed in Ref. 16 using Bz-Lys-Ala-OH as a model peptide along with porcine insulin. The conclusive message was that for the future use of CPD-Y (the serine carboxypeptidase used in the experiments) in transpeptidation reactions it is important to be aware of the possibility that side products may be formed.

For the sake of completeness the enzymatic synthesis of peptide amides by the transacylation mechanism referred to above as "aminolysis of esters" is briefly discussed using the same general symbols as in the above transpeptidation scheme.

The reaction is performed according to the following general reaction scheme

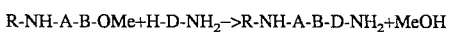

R-NH-A-B-OMe+H-D-NH$_2$->R-NH-A-B-D-NH$_2$+MeOH

The yield of aminolysis is 85–95% for most amino acid amides.

Besides the above investigations of the applicability of serine carboxypeptidases in C-terminal modifications of insulin, a further experiment with amidation of longer peptides using CPD-Y as a catalyst has been reported.

Thus in EP-B2-197794 and the parallel U.S. Pat. No. 4,709,014 (Tamaoki) human calcitonin-Leu peptide was reacted with ammonia as the nucleophile using CPD-Y as the catalyst under conditions otherwise similar to those used by Breddam et al in Ref. 15. (The discussion of Ref. 15 above has been limited to the use of amino acid amides as nucleophiles, while in fact the main purpose of the article was to compare various nucleophiles also including ammonia).

Tamaoki obtained human calcitonin amide in a yield of 24.7%, leaving 57% unreacted substrate and 17.2% non-amidated side products (including human calcitonin).

In its more general aspects the Tamaoki patents disclose a process for the preparation of a peptide having a C-terminal proline amide, which comprises reacting in aqueous solution a peptide substrate having C-terminal Pro-Leu, Pro-Ile, Pro-Val or Pro-Phe with carboxypeptidase Y in the presence of ammonia.

Without in any way wanting to endorse the statements made by Tamaoki, it should be mentioned that he claims that contrary to the findings of Breddam et al in Ref. 15, where a preference for hydrophilic C-terminal amino acids as leaving groups is expressed, the use of hydrophobic amino acids (Leu, Ile, Val and Phe) gives better yields than Gly, when Pro is the penultimate amino acid.

Nevertheless the yields of the amidation products in Tamaoki's examples using Cbz-Ala-Pro-X-OH as the substrate, where X is Leu, Val, Phe and Ile, respectively, were only 35.1%, 43%, 15.4%, 13.4%, 22.6%, respectively. The remainder was—to the extent reported—unreacted starting material and non-amidated side-products Cbz-Ala-Pro-OH.

The present invention is based on the surprising finding that by using a particular type of nucleophile components in the enzyme catalyzed condensation or transacylation processes generally described above, viz. amino group containing compounds susceptible to cleavage leaving an α-amido group on the C-terminal of the formed peptide, and subjecting the peptide to such cleavage, peptide amides may be formed in high yields and excellent purity. The process therefore lends itself perfectly to bulk scale production of peptide amides by modification of peptides, which have been made by genetic engineering.

Consequently, the invention relates to a process for the preparation of C-terminally amidated peptides

P-NH$_2$ wherein P is a peptide residue which may be N-protected by reacting a substrate component selected from a) C-terminally unblocked peptides of the formula

P-OH where P is as defined above b) peptides or peptide derivatives of the formula

P-X-Y where P is as defined above, X is an amino acid residue or a peptide residue and Y is OH, OMe or any other suitable C-terminal modification, and c) C-terminally esterified peptides of the formula

P-OR' where P is as defined above and R'represents alkyl, aryl, heteroaryl, aralkyl or an α-des amino fragment of an amino acid with a nucleophile component in the presence of an enzyme capable of catalyzing the incorporation of the nucleophile, in an aqueous reaction medium, in an organic solvent or a mixture thereof, at a pH sufficient to maintain the enzyme activity, and the process is characterized by using as nucleophile component an amino group containing compound NH$_2$-R which is cleavable so that the reaction product P-NH-R can be converted into P-NH$_2$ and subsequently subjecting the reaction product to such cleavage.

Consequently, the nucleophile NH$_2$-R may be incorporated in three types of enzymatically catalyzed reactions:

(a) condensation reactions

P-OH+NH$_2$-R⇌P-NH-R+H$_2$O

P=peptide residue, which may be N-protected, NH$_2$-R= cleavable nucleophile leaving a C-terminal amide group on the preceeding amino acid residue, i.e. forming P-NH$_2$ in a subsequent reaction.

Such reactions are catalysed by all types of proteases, i.e. aspartic-proteases, metallo-proteases, serine-proteases and thiol proteases, both exopeptidases, e.g. CPD-Y, and endopeptidases, e.g. trypsin and thermolysin (as generally described in U.S. Pat. No. 4,339,534 and the corresponding DK patent No. 155613, i.e. with reference to EP 17938 (Morihara) which reacted des B-30 insulin with an excess amount of a threonine derivative in the presence of trypsin under formation of human insulin.). The equilibrium of such a condensation reaction is normally shifted to the left in aqueous solution unless very high concentrations of the reactants are used. However, addition of solvents may change the equilibrium constant such that a higher yield of product is obtained. Precipitation of the product in the reaction medium can also shift the reaction in favour of the product.

(b) transpeptidation reactions

P-X-Y+NH$_2$-R→P-NH-R+H-X-Y

P and NH$_2$R are defined as in (a). X=amino acid residue or peptidyl, Y=OH, O-alkyl, e.g. OMe or any other suitable C-terminal modification of X.

Such reactions are catalysed by thiol and serine proteases, both exopeptidases, e.g. CPD-Y as explained above, and endopeptidases, e.g. trypsin. In case a carboxypeptidase is used, X=amino acid residue and Y=OH. In case an endopeptidase is used X and Y are as defined above.

(c) aminolysis of peptide and amino acid esters

P-OR$^1$+NH$_2$-R→P-NH-R+HO-X

P and NH$_2$-R are defined as in (a) R$^1$=alkyl, aryl, heteroaryl, aralkyl or an α-desamino fragment of an amino acid.

Such reactions are catalysed by thiol and serine proteases, both exopeptidases, e.g. CPD-Y (as explained above), and endopeptidases, e.g. trypsin.

The selection of the most appropriate of the above three reaction types can be made by the person skilled in the art based especially on the amino acid sequence of the peptide and the specificity of the available enzymes.

If the peptide can easily be converted to an ester, the "aminolysis of esters" is normally preferable.

This esterification may create difficulties, particularly if the peptide contains acidic amino acids, e.g. Glu or Asp, since their free carboxy groups would then also be esterified. In these cases a transpeptidation type reaction might therefore be the best choice.

Generally speaking the person skilled in the art will be able to select the proper reaction type based on experiments with model peptides.

The same goes for the selection of the nucleophile. Once a proper enzyme and reaction type has been chosen, one would preferably select a nucleophile with a suitable pKa such that the nucleophilic amino group is partially or completely deprotonated within the optimal pH-range for the enzyme in the given reaction. Again a proper selection may be made by experiments.

By the same token, if the use of a particular nucleophile is desired, e.g. because it is easy to cleave from the reaction product, an enzyme and a reaction type may be chosen where the pH-conditions are adapted to the pKa of the nucleophile.

Preferred nucleophiles include nucleophiles with the general formula

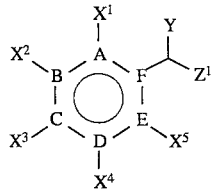

1A wherein A–F represent carbon atoms or up to two nitrogen atoms. Y represents H, straight chain or branched ($C_1$–$C_6$) alkyl, aryl ($R^2$) or aralkyl ($CH_2R^2$ or $CHR^2R^3$). $R^2$ and $R^3$ are aryl groups, which may be substituted with halogen, hydroxy, alkoxy, nitro, amino or alkyl. Alternatively Y represents an oxo group, a carboxy group, or a functional derivative of a carboxy group, eogo an ester, a nitrile, an amide which may be substituted on N with ($C_1$–$C_6$) alkyl, aryl ($R^2$) or aralkyl ($CH_2R^2$ or $CHR^2R^3$), where $R^2$ and $R^3$ are as defined above. $X^1$–$X^5$ independently represent H, ($C_1$–$C_3$) alkyl, halogen, cyano, methoxy, hydroxy, sulfo, amino or nitro, or any two of them may join to form a fused aliphatic or aromatic ring and when any of A-E is nitrogen, the corresponding X is void or is oxygen. $Z^1$ represents amino or an amine derivative of the general formula

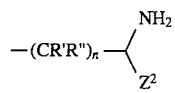

(n = {0, 1, . . . , 5})

wherein $Z^2$ is as defined for Y except for an oxo group, R' and R" are as defined for Y.

Also preferred are nucleophiles of the general formula

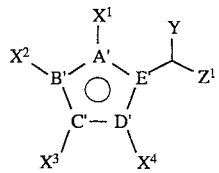

2 wherein A'-E' represent carbon atoms, or one of A'-E' is an oxygen or sulphur atom or up to two of A'-E' are nitrogen atoms. Y, $Z^1$ and $X^1$–$X^4$ are as defined above, and when any of A'-E' are nitrogen, the corresponding X is void or is oxygen and when any of A'-E' is oxygen or sulphur, the corresponding X is void.

More preferred nucleophiles include 2-nitroarylmethylamine derivatives of the general formula

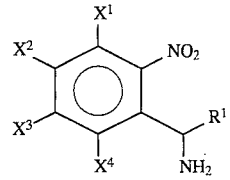

1B wherein $R^1$ represents H, straight chain or branched ($C_1$–$C_6$) alkyl, aryl ($R^2$) or aralkyl ($CH_2R^2$ or $CHR^2R^3$), wherein $R^2$ and $R^3$ are aryl groups, which may be substituted with halogen, hydroxy, alkoxy, nitro, amino or alkyl. Alternatively, $R^1$ represents a carboxy group, or a functional derivative of a carboxy group, e.g. an ester, a nitrile, an amide which may be substituted on N with ($C_1$–$C_6$) alkyl, aryl ($R^2$) or aralkyl ($CH_2R^2$ or $CHR^2R^3$), where $R^2$ and $R^3$ are as defined above. $X^1$–$X^4$ independently represent H, ($C_1$–$C_3$) alkyl, halogen, cyano, methoxy, hydroxy, sulfo or nitro, or any two of them may join to form a fused aliphatic or aromatic ring.

Also included as more preferred nucleophiles are benzylamine derivatives of the general formula

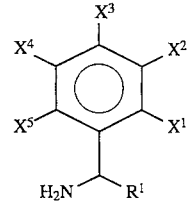

1C wherein $R^1$ is as defined above and $X^1$–$X^5$ independently represent H, ($C_1$–$C_3$) alkyl, halogen, hydroxy, ($C_1$–$C_3$) alkoxy, nitro, sulfo, cyano or carboxy.

In case the cleavage is to be induced following rearrangement as further described below, an allyl amine may be used as the nucleophile. These amines include derivatives of allylamine with the general formula

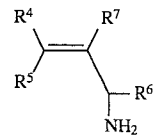

wherein $R^4$–$R^7$ represents H, straight chain or branched ($C_1$–$C_6$) alkyl, aryl ($R^2$) or aralkyl $CH_2R^2$ or $CHR^2R^3$), wherein $R^2$ or $R^3$ are aryl groups, which may be substituted with halogen, hydroxy, alkoxy, nitro, amino or alkyl. Alternatively, $R^4$–$R^7$ represents a carboxy group, or a functional derivative of a carboxy group, e.g. an ester, a nitrile, an amide which may be substituted on N with ($C_1$–$C_6$) alkyl, aryl ($R^2$) or aralkyl ($CH_2R^2$ or $CHR^2R^3$), where $R^2$ and $R^3$ are as defined above.

All these compounds may be reacted with the above-mentioned substrate component in a condensation or transacylation reaction under formation of a C-terminal modified peptide which may be transformed to a peptide amide.

In Ref. 7 carboxypeptidase Y catalyzed reactions between a common acyl component (Bz-Ala-OMe) and a variety of amine compounds are described. The α-amino acid amides tested were—with the exception of isoglutamine—incorporated in high yields (70–95%). Glycinonitril, glycine-N-methylamide and threonine-N-methylamide reacted in low yields (<20%) only. None of the secondary amines tested (sarcosine, sarcosine methyl ester, N-methyl-alanine, proline and proline amide) were incorporated to form an amide bond. However, several structurally interesting primary amines (e.g. L-alaninol, cyclopropylamine, β-alanine amide, taurine, etc.) reacted in good yields (40–60%). Benzyl amine reacted in 65% yield, at a concentration of 0.1M. At higher concentrations (0.5M) there was no turnover, since apparently the formation of an acyl-enzyme intermediate was inhibited. While it has been shown that some amines were applicable as nucleophile components in enzymatic peptide synthesis, no reference is made to a subsequent cleavage of the aminolysis product leaving an amido group on the C-terminal.

The cleavage of the reaction product may be induced inter alia in the following manners:
(a) by photolysis
(b) by solvolysis
(c) by reduction
(d) by rearrangement
(e) by oxidation

(a) PHOTOLYSIS

The peptide to be photolyzed is placed in solution in water, possibly mixed with other solvents like dimethylformamide, hexamethylphosphortriamide, dimethylsulfoxide, lower alcohols, ethylene glycol or diethylene glycol ethers, etc., and irradiated with electromagnetic radiation. In a preferred embodiment, the light has wavelengths longer than 300 nm and shorter than 500 nm, but the useful range of wavelengths will be dependent on the substituents of the clearable group. In a preferred embodiment of the invention, a mildly reducing agent (e.g. sodium hydrogen sulfite) is added before irradiation in order to reduce strongly colored by-products from the photolysis which may react with the substrates or the products or act as internal filter.

Photolysis has earlier been used in connection with solid-phase and liquid-phase peptide synthesis for the removal of C-terminal peptide amides from the resins used as supports in the solid-phase synthesis or from the polyethylene glycol (PEG) used as support in liquid-phase synthesis.

Rich, D. H. and Gurwara, S. K. (1975), Tetrahedron Letters 301–304 (Ref. 4) synthesized polystyrene resin having a 3-nitro-4-amino-methylbenzoylamide anchoring group:

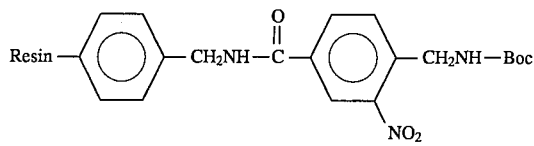

After removal of the Boc-group with 50% TFA/CH$_2$Cl$_2$ followed by neutralization with TEA in CH$_2$Cl$_2$, Boc-Gly and Boc-Val was coupled with the resin.

The protected amino acid amides Boc-Gly-NH$_2$ and Boc-Val-NH$_2$ were liberated from the anchoring group upon photolysis of the resin. The resin was suspended in methanol and irradiated at 350 nm in the absence of oxygen. The protected amides were isolated in quantitative yields, which establish that hindered amino acid derivatives can be removed efficiently from the resin under mild conditions. In another experiment the decapeptide LH-RH was prepared according to the classical Merrifield-solid phase synthesis using the above resin as support. The protected decapeptide resin was photolyzed as described above liberating the protected decapeptide amide.

These results establish that the particular resin can be used in solid-phase synthesis of protected peptides as the C-terminal amides. Hindered C-terminal amino acids are removed under normal photolysis condition.

The authors therefore conclude that the resin is useful for the synthesis of C-terminal peptide amides which are difficult to remove from the classical Merrifield resins under mild conditions.

In a very recent article Ajayagosh, A. and Pillai, V. N. R. (1990), J. Org. Chem. 55, 2826–2829 (Ref. 1) reports the use of similar photolabile o-nitrobenzyl anchoring groups for solid-phase synthesis of peptide-N-alkylamide. The rationale for this work is that peptide N-alkylamides in a number of cases have been observed to be more active than the parent peptide amide.

In other experiments reported by Pillai, V. N. R., Mutter, M. and Bayer, E. (1979), Tetrahedron Letters 3409–3412 (Ref. 2) and Pillai, V. N. R., Mutter, M. (1980), J. Chem. 45, 5364–5370 (Ref. 3) the 3-nitro-4-aminomethyl benzoyl anchoring group was attached to polyethylene glycol and used as support in liquid-phase peptide synthesis.

Also in this method it was possible to release peptide amides from the photolabile anchoring group by photolysis and the authors conclude that several methodological improvements to liquid-phase synthesis on PEG supports are provided. In particular a new soluble polymeric support which permits synthesis and final photolytic removal of peptide amides under neutral conditions was developed.

Furthermore, as described by Wang, S. -S. (1976) J. Org. Chem., 41, 3258–3261 (Ref. 5) other photolabile groups may be used in solid or liquid phase peptide chemistry, e.g.

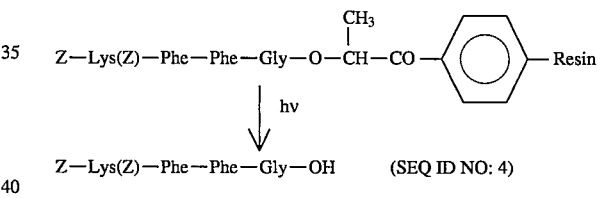

Based on the above articles it can be concluded that it is known to use photolabile anchoring groups for peptide amides in the classical solid-phase and liquid-phase peptide synthesis. However, it has not earlier been suggested to use photolabile amine compounds as the nucleophile in enzymatic peptide synthesis with a view to obtain peptide amides by C-terminal modification following a photolyric cleavage of the reaction product. Also it could not be expected with any certainty that the claimed compounds would act as nucleophiles in the enzymatic peptide synthesis and that both the incorporation of the nucleophile and the subsequent cleavage would proceed with high yields.

(b) SOLVOLYSIS

The peptide to be solvolyzed is suspended or preferably dissolved in an acid, or an acid medium, e.g. trifluoroacetic acid (TFA) or TFA containing various amounts of water and left until all or a sufficiently large amount of the starting material has disappeared. The reaction mixture is subsequently treated in such a way as to remove the cleaved off by-product, e.g. by filtration, and the generated peptide amide is purified if necessary by standard methods.

Solvolysis is a well known method for cleavage of peptides generated by solid or liquid phase peptide synthesis from the resins used as supports in the solid phase synthesis or from the polyethylene glycol used as support in liquid phase synthesis. The use of 2,4-dimethoxybenzhydrylamine resins in this connection is described by Penke, B., and Rivier, J. (1987), J. Org. Chem., 52, 1197–1200 (Ref. 6).

(c) REDUCTION

The peptide to be reduced is suspended or dissolved in a suitable solvent, e.g. acetic acid or aqueous acetic acid, methanol or aqueous methanol, a catalyst is added followed by subjection of the reaction mixture to hydrogen at a pressure between 1 Atm and 200 Atm, or another hydrogen donor may be employed, e.g. formic acid, possibly at elevated temperatures. After uptake of the required amount of hydrogen, the catalyst is removed and the generated peptide amide is purified by standard methods. Furthermore, electrochemical or metal/acid mediated reduction may be employed.

(d) REARRANGEMENT

By using an allyl amine as the nucleophile a reaction product is obtained which may be transformed to a peptide amide by rearrangement and subsequent hydrolysis. The allylamine has the general formula

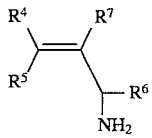

wherein $R^4$–$R^7$ represents H, straight chain or branched ($C_1$–$C_6$) alkyl aryl ($R^2$) or aralkyl $CH_2R^2$ or $CHR^2R^3$), wherein $R^2$ or $R^3$ are aryl groups, which may be substituted with halogen, hydroxy, alkoxy, nitro, amino or atkyl. Alternatively, $R^4$–$R^7$ represents a carboxy group, or a functional derivative of a carboxy group, e.g. an ester, a nitrile, an amide which may be substituted on N with ($C_1$–$C_6$) alkyl, aryl ($R^2$) or aralkyl ($CH_2R^2$ or $CHR^2R^3$), where $R^2$ and $R^3$ are as defined above. The peptide to be rearranged is suspended or preferably dissolved in water or a mixture of water and an organic solvent, or an organic solvent, e.g. an alkanol, dimethylformamide, hexamethylphosphortriamide, dimethylsulfoxide dioxane or pyridine, etc. Subsequently a catalyst is added, like e.g. triethylamine, lithium oxide, lithium sulfide, etc. The mixture is reacted for 1–48 hours, after which the resulting peptide amide is purified by standard methods.

(e) ELIMINATION

By using an amine as nucleophile a reaction product is obtained which may be transformed to a peptide amide by elimination.

Nucleophiles in this category are preferably compounds that after insertion in the C-terminal of the peptide can be removed in a 1,2-, 1,4- or 1,6-elimination reaction These nucleophiles include allylamines with the general formula

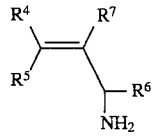

wherein $R^4$–$R^7$ represents H, straight chain or branched ($C_1$–$C_6$) alkyl aryl ($R^2$) or aralkyl $CH_2R^2$ or $CHR^2R^3$), wherein $R^2$ or $R^3$ are aryl groups, which may be substituted with halogen, hydroxy, alkoxy, nitro, amino or alkyl. Alternatively, $R^4$–$R^7$ represents a carboxy group, or a functional derivative of a carboxy group, e.g. an ester, a nitrile, an amide which may be substituted on N with ($C_1$–$C_6$) alkyl, aryl ($R^2$) or aralkyl ($CH_2R^2$ or $CHR^2R^3$), where $R^2$ and $R^3$ are as defined above.

In a preferred form of experiment highly conjugated β-amino acid derivatives are enzymatically inserted in the peptide which is subsequently subjected to an acid/ or base catalyzed 1,2-elimination which produces a peptide amide.

In another preferred form of experiment hydroxy benzylamine derivatives inserted in the peptide can be subjected to a base catalyzed 1,6-elimination resulting in formation of the peptide amide.

(f) OXIDATION

The peptide to be oxidized is suspended or preferably dissolved in water or a mixture of water and an organic solvent. Subsequently a relatively mild oxidizer is added, like e.g. hydrogen peroxide, chloramine-T or immobilized chloramine (Iodobeads). As soon as the oxidation is finished, excess oxidant is destroyed or removed, and the resulting peptide amide is purified by standard methods.

The leaving group on the substrate component should be selected in accordance with the enzymatic properties of the enzyme used.

Preferred enzymes at present are serine carboxypeptidases, but also serine- or thiol-endoproteases or other proteases may be used, if the necessary measures are taken to avoid internal cleavage of the reaction products.

As mentioned above serine carboxypeptidases are capable of catalyzing both aminolysis of esters, in which case the leaving group should be an alcohol group and transpeptidation in which case the leaving group is a free amino acid.

The preferred carboxypeptidases in the process of the invention are L-specific serine or thiol carboxypeptidases. Such enzymes can be produced by yeast fungi, or they may be of animal, vegetable or other microbial origin.

A particularly expedient enzyme is carboxypeptidase Y from yeast fungi (CPD-Y). This enzyme is described in the earlier patents i.a. with reference to Johansen et al (Ref. 28) who developed a particularly expedient purification method by affinity chromatography on an affinity resin comprising a polymeric resin matrix with coupled benzylsuccinyl grups. CPD-Y, which is a serine enzyme is available in large amounts and displays a high stability. Further details are given in Ref. 14.

In addition to CPD-Y, which is the preferred enzyme at present, the process of the invention is feasible with other carboxypeptidases, such as those listed in the following survey:

| Enzyme | Origin |
| --- | --- |
| | Fungi |
| Carboxypeptidase S-1 | *Penicillium janthinellum* |
| Carboxypeptidase S-2 | *Penicillium janthinellum* |
| Carboxypeptidase(s) from | *Aspergillus saitoi* |
| Carboxypeptidase(s) from | *Aspergillus oryzae* |
| | Plants |
| Carboxpeptidase(s) C | Orange leaves |
| | Orange peels |
| Carboxypeptidase $C_N$ | Citrus natusdaidai Hayata |

| Enzyme | Origin |
| --- | --- |
| Phaseolain | French bean leaves |
| Carboxypeptidases M-I and M-II | Germinating berlay |
| Carboxypeptidase W-II | Wheat bran |
| Carboxypeptidases from | Germinating cotton plants |
| | Tomatoes |
| | Watermelons |
| | Bromelain (pineapple) powder |

The close relationship between a number of the above carboxypeptidases is discussed by Kubota et al (Ref. 33).

Another type of applicable enzymes are dipeptidyl peptidases which cleave a dipeptide from the C-terminal.

In connection with the above discussion of reactions (a), (b) and (c) a number of applicable enzymes has been suggested.

Generally speaking, the person skilled in the art will be able to select a suitable enzyme based on the known specificities for particular amino acids or substrates, the structure of the desired peptide amide, etc.

The process of the invention may be carried out at pH 3–11 depending on the enzyme used. The preferred pH-value, which is often within a very narrow range, depends upon the enzyme used and of the type of reaction aimed at, viz. (a), (b) or (c) as discussed above.

The selected pH-value should preferably be maintained throughout the reaction.

The pH-control may be provided for by incorporating a suitable buffer for the selected pH-range in the reaction medium.

The pH-value may also be maintained by adding an acid, such as HCl, or a base, such as NaOH, during the reaction. This may conveniently be done by using a pH-stat.

However, the conditions may also be influenced upon by varying the enzyme concentration, reaction time, etc.

Depending particularly on the enzyme and the reactants, the reaction is carried out in an aqueous reaction medium or a mixture of water and an organic solvent, or in an organic solvent. Preferred organic solvents are alkanols, e.g. methanol and ethanol, glycols, e.g. ethylene glycol or polyethylene glycols, glycerol, alkanoic acids, e.g. acetic acid, dimethyl formamide, dimethyl sulfoxide, tetrahydrofurane, dioxane and dimethoxyethane.

The selection of the composition of the reaction medium depends particularly upon the solubility, temperature and pH of the reaction components and the reaction products involved and upon the stability of the enzyme.

The reaction medium may also comprise a component that renders the enzyme insoluble, but retains a considerable part of the enzyme activity, such as an ion exchanger resin. Alternatively, the enzyme may be immobilized in known manner, e.g. by bonding to a matrix, such as a cross-linked dextran or agarose, or to a silica, polyamide or cellulose, or by encapsulating in polyacrylamide, alginates or fibres. Besides, the enzyme may be modified by chemical means or site directed mutagenesis or other genetic means to improve its stability or enzymatic properties.

Additives like chelating agents, e.g. EDTA, metal ions and salts are included in the reaction medium depending on the requirements of the enzyme salts.

The concentration of the two participants in the reaction may vary within wide limits, as explained below. A preferred starting concentration for the substrate component is 0.1–20 mM, preferably 1–10 mM, and for the nucleophile component 0.001 to 2M, preferably 0.025 to 1.5M, in particular 0.1–1.0M.

The enzyme concentration may vary as well, but the concentration is preferably $10^{-8}$ to $10^{-4}$M. The most advantageous activity depends i.a. on the substrate chain and concentration, the nucleophile concentration, the reaction time, the reaction temperature, the pH, and the presence of organic solvents and/or salts.

According to the invention the reaction temperature is −30° to 80° C., preferably 20° to 40° C. The most appropriate reaction temperature for a given synthesis can be determined by experiments. An appropriate temperature will usually be about 20° to 37° C., preferably about 25° C., taking into account due consideration for enzyme activity and stability.

Similar variations occur for the reaction time which depends very much upon the other reaction parameters, especially the enzyme concentration. The standard reaction time in the process of the invention is about 1–3 hours.

The abbreviations of amino acids, amino acid derivatives and peptides are according to Guidelines of the IUPAC-IUB Commission on Biochemical Nomenclature and the amino acids are on L-form unless otherwise stipulated.

The following additional abbreviations are used: AcOH, acetic acid; MeOH, methanol; Bz, N-benzoyl; Boc, tert.butoxycarbonyl; DMF, N,N-dimethylformamide; EDTA, ethylene diamine-N,N,N',N'-tetraacetic acid; HPLC, High Performance Liquid Chromatography; TLC, Thin Layer, Chromatography; TFA, trifluoro acetic acid; THF, tetrahydrofuran, TEA, triethylamine; TEAP, triethylammonium phosphate.

Before the process of the invention will be illustrated by examples, starting materials, apparatus methods of measurement, etc. will be explained in general terms.

In a number of examples N-substituted benzamides were used as models to illustrate the invention, where benzamide was the expected product. These were prepared by standard procedures. Furthermore, the peptides used to demonstrate the invention were often labelled with a benzoyl group at the N-terminus, in order to make their detection by the HPLC and UV detector easier.

CHEMICALS

CPD-Y courtesy of Carlsberg Ltd. (Klaus Breddam). Z-Gly-Ala-Pro-Ala-OH (SEQ ID NO:8), Z-Gly-Ala-Pro-NH$_2$ (SEQ ID NO:11), Tyr-Gly-Trp-Met-Asp-Phe-Ala-OH, Tyr-Gly-Trp-Met-Asp-Phe-NH$_2$, Pro-Gln-Thr-Ala-Ile-Gly-Val-Gly-Ala-Pro-Ala-OH (SEQ ID NO:12) and Pro-Gln-Thr-Ala-Ile-Gly-Val-Gly-Ala-Pro-NH$_2$ (SEQ ID NO:12) were prepared by standard solid-phase peptide synthesis.

2-Nitrophenylglycine amide and 3-(2,4-dimethoxyphenyl)-3-propionic acid amide were prepared as outlined in example 1 and 10, respectively, Acetonitrile (HPLC-grade, RH 1015) from RATHBURN. All other chemicals are from Aldrich. Other organic solvents for HPLC were distilled before use.

| APPARATUS | |
|---|---|
| pH measurements: | Radiometer (Copenhagen) pH Meter 28 |
| | Electrode GK 2421C (Radiometer, Glass electrode) |
| HPLC system: | Waters 994 Programmable Photodiode Array Detector |
| | Waters 600E Multisolvent Delivery System |
| | Waters 5200 Printer Plotter |
| Photolysis: | Bausch & Lomb Mercury Light Source SP200 |
| | Bausch & Lomb Mercury Power Aupply SP200 |

HPLC SOLVENT SYSTEM

| System 1: | Buffer A: | 50 mM TEAP[1], pH ~ 3.0, containing 10% (v/v) $CH_3CN$ | |
|---|---|---|---|
| | Buffer B: | $CH_3CN$ containing 20% (v/v) buffer A. | |
| | Gradient: | t (min)   % A | % B |
| | | 0   60 | 40 linear |
| | | 10   0 | 100 linear |
| | | 15   60 | 40 |

| System 2: | Buffer A: | 50 mN TEAP, pH ~ 3.0 containing 10% (v/v) $CH_3CN$ | |
|---|---|---|---|
| | Buffer B: | $CH_3CN$ containing 20% (v/v) buffer A | |
| | Gradient: | t (min)   % A | % B |
| | | 0   100 | 0 concave |
| | | 5   60 | 40 linear |
| | | 8   100 | 0 |

| System 3: | Buffer A: | 50 mM TEAP, pH ~ 3.0 containing 10% (v/v) $CH_3CN$ | |
|---|---|---|---|
| | Buffer B: | $CH_3CN$ containing 20% (v/v) buffer A | |
| | Isocratic. | % A | % B |
| | | 60 | 40 |
| | Flow: | 1.5 ml/min. | |

| System 4: | Buffer A: | $H_2O$ containing 0.1% (v/v) trifluoro-acetic acid (TFA) | |
|---|---|---|---|
| | Buffer B: | $CH_3CN$ containing 10% (v/v) $H_2O$ and 0.2% (v/v) TFA | |
| | Isocratic: | % A | % B |
| | | 80 | 20 |
| | Flow: | 1.5 ml/min. | |

| System 5: | Buffer A: | $H_2O$ containing 0.1% (v/v) trifluoro-acetic acid (TFA) | |
|---|---|---|---|
| | Buffer B: | $CH_3CN$ containing 10% (v/v) $H_2O$ and 0.1% (v/v) (TFA) | |
| | Isocratic: | % A | % B |
| | | 70 | 30 |
| | FLow: | 2 ml/min | |

| System 6: | Buffer A: | $H_2O$ containing 0.1% (v/v) trifluoro-acetic acid (TFA) | |
|---|---|---|---|
| | Buffer B: | $CH_3CN$ containing 10% (v/v) $H_2O$ and 0.1% (v/v) (TFA) | |
| | Gradient: | t (min)   % A | % B |
| | | 0   80 | 20 |
| | | 5   60 | 40 |
| | | 10   60 | 40 |
| | | 12   80 | 20 |
| | Flow: | 2 ml/min | |

| System 7: | Buffer A: | $H_2O$ containing 0.1% (v/v) tirfluoro-acetic acid (TFA) |
|---|---|---|
| | Buffer B: | $CH_3CN$ containing 10% (v/v) $H_2O$ and 0.1% (v/v) (TFA) |

| Gradient: | t (min) | % A | % B |
|---|---|---|---|
| | 0 | 60 | 40 |
| | 3 | 60 | 40 |
| | 7 | 40 | 60 |
| | 10 | 40 | 60 |
| | 12 | 60 | 40 |
| Flow: | 2 ml/min | | |

[1]0.5 M Triethylammonium phosphate buffer: 900 ml $H_2O$ containing 33.7 ml orthophosphoric acid (85%). Titrated with triethylamino to pH ~ 3.0. Add $H_2O$ to 1000 ml.

EXAMPLE 1

Preparation of N-benzoyl-2-nitrophenylglycine amide (model compound) and photolyric cleavage A) Preparation of 2-nitrophenylglycine amide 2-Nitrophenylacetic acid (36.2 g, 0.2 mol) was suspended in thionyl chloride (30 ml, 0.4 mol) and stirred for 16 h at 20° C. The reaction mixture was evaporated to dryness and suspended in dry chloroform (100 ml). To this solution was added N-bromosuccinimide (50 g, 0.28 mol), dibenzoyl peroxide (10 mg) as catalyst and it was refluxed for 48 h. The reaction mixture was evaporated to dryness, suspended in dry ether, and the precipitated (N-hydroxysuccinimide) was filtered off. The solution was evaporated to dryness and added to cold concentrated ammonium hydroxide (200 ml). The α-bromo-(2-nitrophenyl)acetamide was collected by filtration after 1 h and recrystallized from water/ethanol (4:1 v/v). Yield: 20.0 g (38%); mp 126°–129° C., identified by IR and $^1H$ NMR spectroscopy.

α-Bromo-(2-nitrophenyl)acetamide (4.0 g, 0.02 mol) was suspended in DMSO (4 ml) and treated with $NH_3$; after 2 h the reaction mixture was freeze dried and the product was recrystallized from absolute ethanol. Yield: 2.6 g (68%); mp 116°–120° C., identified by $^1H$ NMR spectroscopy.

B) Preparation of N-Benzoyl-2-nitrophenylglycine amide

2-Nitrophenylglycine amide, 1 DMSO (500 mg, 1.83 mmol) was suspended in chloroform (20 ml) and triethylamine (390 µl, 2.80 mmol) was added. Subsequently benzoyl chloride (330 µl, 2.8 mmol) was added with stirring. The reaction was followed by TLC using as eluent: $CH_2Cl_2$/MeOH/AcOH (85:10:5) and after 1 h at 20° C. the reaction mixture was treated with a saturated solution of $NaHCO_3$, dried over anhydrous $MgSO_4$ and evaporated to dryness. The product was recrystallized from absolute ethanol. Yield: 600 mg (77%); mp 178°–180° C., identified by $^1H$ NMR spectroscopy.

Reaction scheme:

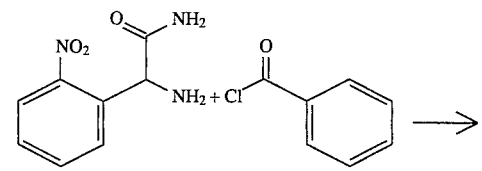

Reaction scheme:
-continued

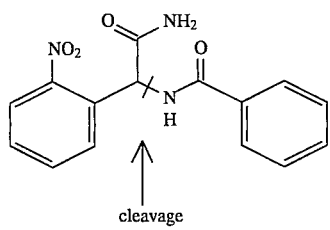

cleavage

C) Photolysis of N-benzoyl-2-nitrophenylglycine amide

N-Benzoyl-2-nitrophenylglycine amide (15 mg, 50 μmol) was dissolved in methanol:water (1:1) (25 ml), and NaHSO₃ (52 mg, 500 μmol) was added. The reaction mixture was purged with nitrogen for 15 min and subsequently photolyzed under nitrogen cover at a distance of 20 cm from the SP 200 lamp through Pyrex. The photolysis was followed by taking out samples at 0, 10, 30 and 60 min. Each sample was analyzed using HPLC system-1 and the results were compared with the 0' test as well as with the chromatogram of a 10 mM benzamide solution in methanol. The generated benzamide was determined quantitatively using benzamide standard chromatograms.

EXAMPLE 2

Preparation of Bz-Ala-NH$_2$ by "aminolysis of esters" and photolyric cleavage

A) Transacylation of Bz-Ala-OMe with 2-nitrophenylglycine amide as nucleophile using enzyme CPD-Y EDTA (2 ml, 5 mM), pH~7.9 was added to 2-nitrophenylglycine amide, 1 DMSO (25 mg), pH was adjusted to ~8.0 with 5N NaOH, and Bz-Ala-OMe (10 gl) of a solution of 207 mg/ml (1M) MeOH was added. A 0' sample was prepared by adding CH$_3$CN (240 ml) to 10 gl reaction mixture. Subsequently CPD-Y (15 μl, 22 mg/ml H$_2$O) was added to the reaction mixture, and the reaction was followed by extracting samples at 15, 30 and 60 min. Each sample was analyzed using HPLC system-3 and the chromatograms compared to those of standard solutions of Bz-Ala-OMe and Bz-Ala-OH, whereby the product distribution was determined. At t=75 min, 0.1N HCl was added until pH corresponded to 2.0. The reaction mixture was extracted with CHCl$_3$ (3×2 ml) and the chloroform phase was dried over MgSO$_4$ and evaporated. The residue was dissolved in methanol and analyzed using HPLC system-3, which showed that the residue contained ~100% transacylation product which was identified by mass spectrometry as Bz-Ala-2-nitrophenylglycine amide, M$_{wt}$=370.

B) Photolysis of Bz-Ala-2-nitrophenylglycine amide

Bz-Ala-2-nitrophenylglycine amide (95 mg) purified by semipreparative HPLC as described above was dissolved in MeOH/H$_2$O (25 ml, 1:1), and NaHSO$_3$ (52 mg, 0.62 mmol) was added to quench the generated 2-nitrosophenylglycolamide which would otherwise form a powerful inner filter, which could reduce the peptide amide yield. The reaction mixture was purged with nitrogen for 15 min and subsequently photolysed with nitrogen cover a distance of 20 cm from the SP 200 lamp through Pyrex. After 30, 60 and 90 min samples were taken out and analyzed using HPLC system-1. The results were compared with that from the starting material and the chromatogram of 1 mM Bz-Ala-NH$_2$ prepared from Bz-Ala-NHS and 25% aqueous ammonia. The photolysis mixture was extracted with chloroform (2×10 ml). 0.5N NaOH was added to the aqueous phase until pH ~9.0 and it was subsequently extracted with chloroform (2×20 ml). The chloroform phase was dried over MgSO$_4$ and evaporated. The residue was dissolved in MeOH/H$_2$O (1:1) and analyzed using HPLC system-1. The residue was found to contain ~100% Bz-Ala-NH$_2$. The reaction product was identified using UV spectroscopy, HPLC chromatograms and mass spectrometry.

EXAMPLE 3

Preparation of Bz-Ala-NH$_2$ by "aminolysis of as nucleophile ester" and photolyric cleavage A) Transacylation of Bz-Ala-OMe with 2-nitrobenzylamine as nucleophile using CPD-Y 2-Nitrobenzylamine, HCl (94 mg) was added to 5 mM EDTA (2 ml, pH ~8.0), pH was adjusted to 8.0 with 5N NaOH, and Bz-Ala-OMe (20 μl, 207 mg/(ml MeOH)) was added. A 0 sample was prepared by adding CH$_3$CN (240 μl) to 10 μl of the reaction mixture. Subsequently CPD-Y (15 μl, 22 mg/ml H$_2$O) was added, and the reaction was followed by extracting and analyzing samples at 5, 60, 120 and 300 min. Each sample was analyzed using HPLC system-6 and the chromatograms compared to standard solutions of Bz-Ala-OMe and Bz-Ala-OH whereby the product distribution was determined, (the transacylation product yield was >90%). The reaction product was identified using mass spectrometry as Bz-Ala-2-nitrobenzylamide, M$_{wt}$=305.

B) Photolysis of Bz-Ala-2-nitrobenzylamide

Bz-Ala-2-nitrobenzylamide (1.5 mg) in MeOH (1.0 ml) was added to NaHSO$_3$ (6.2 mg) (dissolved in 1.0 ml water) and pH was adjusted to 9.5 with 5N NaOH. The reaction mixture was purged with nitrogen for 15 min and subsequently photolysed with nitrogen cover at a distance of 20 cm from the SP 200 lamp through Pyrex. The reaction was followed by extracting and analyzing samples at 0, 1, 5, 10 and 30 min. Each sample was analyzed using HPLC system-6 and the chromatograms compared with those of a 10 mM standard solution of Bz-Ala-NH$_2$. The reaction product (yield >95%) was further identified using mass spectrometry.

EXAMPLE 4

Preparation of Bz-Gly-Ala-Pro-2-nitrophenylglycine (SEQ ID NO:13) amide by transpeptidation A) Hydrolysis of Bz-Gly-Ala-Pro-Ala-OH (SEQ ID NO:14) with CPD-Y EDTA (95 μl, 5 mM), pH ~6.5 (prepared as follows: 146 mg EDTA was dissolved in 2.0 ml 2N NaOH, pH adjusted to 6.5 with 4 N HCl and H$_2$O added to 100 ml) was added to 100 mM Bz-Gly-Ala-Pro-Ala-OH (SEQ ID NO:14) (5 μl, 41 mg/ml DMF) and pH was adjusted to 6.5 with 5N NaOH. As a 0' test 10 μl of the reaction mixture was added to 200 μl of CH$_3$CN. After this CPD-Y (10 μl, 22 mg/ml H$_2$O) was added to the reaction mixture, and the reaction was followed by extracting 10 μl samples at 1, 5, 10 and 20 min. CPD-Y was denatured by adding CH$_3$CN (200 μl) to each sample. Each sample was analyzed using HPLC system-2 and the chromatograms compared with those of 10 mM standard solutions of Bz-Gly-OH and Bz-Gly-Ala-Pro-Ala-OH, whereby retention times for Bz-Gly-Ala-Pro-OH and Bz-Gly-Ala-OH could be determined.

B) Transpeptidation of Bz-Gly-Ala-Pro-Ala-OH (SEQ ID NO:1) with 2-nitrophenylglycine amide as nucleophile using CPD-Y 70 mM 2-nitrophenylglycine amide (95 µl), pH ~6.5 (prepared as follows: 70 mM 2-nitrophenylglycine amide (1M DMSO/mol, 19.5 mg) was added to 5 mM EDTA (1 ml, pH ~6.5) and pH adjusted to 6.5 with 5N NaOH) was mixed with 100 mM Bz-Gly-Ala-Pro-Ala-OH (SEQ ID NO:14) (5 µl, 41 mg/ml DMF). 0 min test: 10 µl reaction mixture was added to 200 µl CH$_3$CN. Subsequently CPD-Y (15 µl, 22 mg/ml H$_2$O) was added to the reaction mixture. The reaction was followed by extraction of samples at 1, 5, 10, 20, 40, 60, 120 and 180 min. The enzymatic reaction was stopped by adding CH$_3$CN (200 µl) to each sample. The samples were analyzed using HPLC system-2, and the chromatograms were compared with the chromatogram corresponding to 0 min and the results from CPD-Y hydrolysis of Bz-Gly-Ala-Pro-Ala-OH (SEQ ID NO:13). The transpeptidation product was purified using HPLC system-4 and identification performed by determination of retention time, UV, $^1$H NMR and mass spectrometry.

EXAMPLE 5

Preparation of Z-Gly-Ala-Pro-NH$_2$ by transpeptidation and photolytic cleavage

A) Transpeptidation of Z-Gly-Ala-Pro-Ala-OH (SEQ ID NO:8) with 2-nitrophenylglycine amide as nucleophile using CPD-Y 300 mM 2-nitrophenylglycine amide (95 µl ), pH ~6.0 (prepared as follows: 2-nitrophenylglycine amide, DMSO (81.9 mg) was added to 5 mM EDTA (1 ml, pH ~6.5) and pH was adjusted to 6.0 with 5N NaOH) was mixed with 10 mM Z-Gly-Ala-Pro-Ala-OH (SEQ ID NO:13) (5 µl, 4.1 mg/ml DMF). 0' test: 10 µl reaction mixture was added to 200 µl CH$_3$CN. Subsequently CPD-Y (15 µl, 22 mg/ml H$_2$O) was added to the reaction mixture. The reaction was followed by extraction of samples for analysis at 10, 60, 120, 180 min. The enzymatic reaction was stopped by adding CH$_3$CN (200 µl) to each sample. The samples were analyzed using HPLC system-5, and the chromatograms were compared with the chromatogram corresponding to 0 min and the results from CPD-Y hydrolysis of Z-Gly-Ala-Pro-Ala-OH (SEQ ID NO:13). The yield of transpeptidation product was ~100% and it was purified using HPLC system-4. Identification was performed by determination of retention time, UV spectroscopy, $^1$H NMR spectroscopy and by mass spectrometry.

B) Photolysis of Z-Gly-Ala-Pro-2-nitrophenylglycine (SEQ ID NO:13) amide

Z-Gly-Ala-Pro-2-nitrophenylglycine (SEQ ID NO:13) amide (0.025 mmol) in MeOH (12.5 ml) was added to 80 mM NaHSO$_3$ (12.5 ml) and pH was adjsuted to 9.5 with 5N NaOH. The reaction mixture was purged with N$_2$ for 15 min and subsequently photolyzed under nitrogen cover at a distance of 20 cm from the SP 200 lamp through Pyrex. The photolysis was followed by extraction of samples at 0, 30, 60 and 120 min. Each sample was analyzed using HPLC system-5 and the results compared with those from the 0 min sample as well as with the results from the CPD-Y hydrolysis and the transpeptidation mixture. Purification and identification were performed as previously described.

EXAMPLE 6

Preparation of Tyr-Gly-Trp-Met-Asp-Phe-NH$_2$ (SEQ ID NO:11) by transpeptidation and photolyric cleavage A) Transpeptidation of Tyr-Gly-Trp-Met-Asp-Phe-Ala-OH (SEQ ID NO:9) with 2-nitrophenylglycine amide as nucleophile using CPD-Y 300 mM 2-nitrophenylglycine amide (95 µl), pH ~5.5, (prepared as follows: 2-nitrophenylglycine amide, 1 DMSO (81.9 mg) was added to 5 mM EDTA (1 ml, pH ~6.5) and pH was adjusted to 5.5 with 5N NaOH), was mixed with 50 mM Tyr-Gly-Trp-Met-Asp-Phe-Ala-OH (SEQ ID NO:9) (1 µl, 44.4 mg/ml DMF). 0 test: 10 µl reaction mixture was added to CH$_3$CN (200 µl). Subsequently CPD-Y (2 µl, 22 mg/ml water) was added to the reaction mixture. The reaction was followed by extraction of samples for analysis at 10, 60, 120, 180 min. The enzymatic reaction was stopped by adding CH$_3$CN (200 µl) to each sample. The samples were analyzed using HPLC system-5, and the chromatograms were compared with the chromatogram corresponding to 0 min and the results from CPD-Y hydrolysis of Tyr-Gly-Trp-Met-Asp-Phe-Ala-OH (SEQ ID NO:9). The yield of transpeptidation product was ~100% and it was purified using HPLC system-4. Identification was performed by determination of retention time, UV .spectroscopy, amino acid analysis, and mass spectrometry.

B) Photolysis of Tyr-Gly-Trp-Met-Asp-Phe-2-nitrophenyl-glycine (SEQ ID NO:14) amide Tyr-Gly-Trp-Met-Asp-Phe-2-nitrophenylglycine amide (0.025 mmol) in 12.5 ml MeOH was added to 80 mM NaHSO$_3$ (12.5 ml) and pH was adjusted to 9.5 with 5N NaOH. The reaction mixture was purged with N$_2$ for 15 min and subsequently photolyzed under nitrogen cover at a distance of 20 cm from the SP 200 lamp through Pyrex. The photolysis was followed by extraction of samples for analysis at 0, 30, 60 and 120 min. Each sample was analyzed using HPLC system-5 and the results compared with the 0 min sample as well as with the results from the CPD-Y hydrolysis and from the transpeptidation mixture. Purification and identification were performed as previously described.

EXAMPLE 7

Preparation of Pro-Gln-Thr-Ala-Ile-Gly-Val-Gly-Ala-Pro-NH$_2$ by transpeptidation and photolytic cleavage A) Transpeptidation of Pro-Gln-Thr-Ile-Gly-Val-Gly-Ala-Pro-Ala-OH (SEQ ID NO:15) with 2-nitrophenylglycine amide as nucleophile using CPD-Y 220 mM 2-nitrophenylglycine amide (400 µl), pH ~6.0 (prepared as follows: 2-nitrophenylglycine amide, 1 DMSO (60 mg) was added to 5 mM EDTA (1 ml, pH ~6.5) and pH was adjusted to 6.0 with 5N NaOH) was mixed with 50 mM Pro-Gln-Thr-Ala-Ile-Gly-Val-Gly-Ala-Pro-Ala-OH (SEQ ID NO:10) (4.1, 49 mg/ml DMF). 0 min test: 10 µl reaction mixture was added to CH$_3$CN (200 µl). Subsequently CPD-Y (2 µl, 22 mg/ml water) was added to the reaction mixture. The reaction was followed by extraction of samples for analysis of 10, 60, 120, 180 min. The enzymatic reaction was stopped by adding CH$_3$CN (200 µl) to each sample. The samples were analyzed using HPLC system-5, and the chromatograms were compared with the chromatogram corresponding to 0 min and the results from CPD-Y hydrolysis of Pro-Gln-Thr-Ala-Ile-Gly-Val-Gly-Ala-Pro-Ala-OH (SEQ ID NO:10). The yield of transpeptidation product was >90% and it was purified using HPLC. Identification was performed by determination of retention time, UV spectroscopy, amino acid analysis, and mass spectrometry.

B) Photolysis of Pro-Gln-Thr-Ala-Ile-Gly-Val-Gly-Ala-Pro-2-nitrophenylglycine (SEQ ID NO:16) amide Pro-Gln-Thr-Ala-Ile-Gly-Val-Gly-Ala-Pro-2-nitrophenylglycine (SEQ ID NO:12) amide (0.025 mmol) in 12.5 ml MeOH was added to 80 mM NaHSO₃ (12.5 ml) and pH was adjusted to 9.5 with 5N NaOH. The reaction mixture was purged with N₂ for 15 min and subsequently photolyzed under nitrogen cover at a distance of 20 cm from the SP 200 lamp through Pyrex. The photolysis was followed by extraction of samples for analysis at 0, 30, 60 and 120 min. Each sample was analyzed using HPLC system-5 and the results compared with the 0 sample as well as with the results from the CPD-Y hydrolysis and from the transpeptidation mixture. The yield of photolysis product was >70% (HPLC). Purification and identification were performed as previously described.

EXAMPLE 8

Preparation of Bz-Ala-phenacylamide by "aminolysis of ester"

Transacylation of Bz-Ala-OMe with 2-aminoacetophenone as nucleophile using CPD-Y 2-Aminoacetophenone,HCl (17.2 mg) was added to 5 mM EDTA (1 ml, pH ~8.0). pH was adjusted to 8.0 with 5N NaOH, and Bz-Ata-OMe (10 µl, 207 mg/(ml MeOH)) was added. A 0 sample was prepared by adding CH₃CN (240 µl) to 10 µl of the reaction mixture. Subsequently CPD-Y (5 µl, 18 mg/ml H₂O) was added, and the reaction was followed by extracting and analyzing samples at 5, 30, 60 and 120 min. Each sample was analyzed using HPLC system-6 and the chromatograms compared to those of standard solutions of Bz-Ala-OMe and Bz-Ala-OH whereby the product distribution was determined (the transacylation product yield was ~80%). The reaction product was identified using mass spectrometry as Bz-Ala-phenacylamide, $M_{wt}$=310.

EXAMPLE 9

Preparation and solvolysis of benzoylbenzylamine model compounds for solvolytic cleavage A) N-benzoyl-2,4-dimethoxybenzylamine 2,4-dimethoxybenzylamine, HCl (1.02 g, 5.0 mmol) was suspended in pyridine (20 ml) and cooled in an ice bath. Subsequently benzoyl chloride (0.52 ml, 6.5 mol) was added with stirring. The ice bath was removed and the reaction mixture was stirred for 3 h at 20° C. The reaction mixture was extracted with 2×20 ml methylene chloride and the organic layer was treated with 2×10 ml 0.1N NaOH, 3×20 ml 0.5N HCl, 2×20 ml saturated solution of NaCl, dried over anhydrous MgSO₄ and evaporated to dryness.

The product was recrystallized from absolute ethanol. Yield: 760 mg (56%); mp 101°–103° C., identified by 1N NMR spectroscopy.

B) Solvolysis of N-benzoyl-2,4-dimethoxybenzylamine

N-benzoyl-2,4-dimethoxybenzylamine (100 mg, 0.37 mmol) was dissolved in 1 ml 95% (v/v) trifluoroacetic acid (TFA) and stirred for 1 h at 20° C. TFA was removed by blowing with N₂ and the residue suspended in methanol (1 ml). The reaction mixture was analyzed by TLC using CH₂Cl₂/MeOH/AcOH (85:10:5) as eluent and the generated benzamide was determined quantitatively by HPLC using benzamide standard chromatograms.

N-Benzoyl-4-methoxybenzylamine, N-benzoyl-2-methoxybenzylamine and N-benzoyl-3,4-dimethoxybenzylamine were prepared and solvolyzed as described above.

| N-Benzoylbenzylamines | Cleavage with Trifluoroacetic acid (TFA) |
|---|---|
| N-benzoyl-2,4-dimethoxybenzylamine | 95% (v/v) TFA 1 h, quantitative cleavage. |
| N-benzoyl-3,4-dimethoxybenzylamine | 100% (v/v) TFA 20 h, partial cleavage. |
| N-benzoyl-4-methoxybenzylamine | 100% (v/v) TFA 20 h, >50% cleavage. |
| N-benzoyl-2-methoxybenzylamine | 100% (v/v) TFA 20 h, >50% cleavage. |

EXAMPLE 10

Preparation and solvolysis of a propionic amide model compound for solvolytic cleavage A) Preparation of 3-amino-3-(2,4-dimethoxyphenyl)propionic amide A mixture of 2,4-dimethoxybenzaldehyde (21 g, 0.126 mol), malonic acid (20 g, 0.192 mol), ammonium acetate (30 g, 0.39 mol) and ethanol (40 ml) was stirred and heated on a water bath. After refluxing for 4 h the mixture was cooled to 40° C. and the precipitated salt was filtered off and washed with cold ethanol (40 ml). By additional cooling on ice a further crystalline material precipitated, which was isolated and washed with cold ethanol (40 ml) and ether (40 ml). Recrystallisation from ethanol/water 60:40 gave 3-amino-3-(2,4-dimethoxyphenyl)propanoic acid (10.3 g, 38%).

Benzyl chloroformate (2.5 ml, 17.5 mmol) was added dropwise to a solution of 3-amino-3-(2,4-dimethoxyphenyl)propanoic acid (3 g, 14.1 mmol) in 0.2N NaOH (20 ml). The solution was stirred for 2 h and kept basic with additional conc. NaOH. The solution was acidified with conc. HCl whereby Z-3-amino-3-(2,4-dimethoxyphenyl)propanoic acid precipitated. The precipitate was isolated and washed with ether to give (3.9 g, 11.29 mmol, 80%).

A solution of Z-3-amino-3-(2,4-dimethoxyphenyl)propanoic acid (2.3 g, 6.66 mmol) in methylene chloride (20 ml) was cooled on ice and thionyl chloride (0.5 ml, 6.85 mmol) was added. The solution was stirred for 1 h at room temperature, filtrated and evaporated to dryness under reduced pressure. The residue was dissolved in methylene chloride (20 ml) and stirred vigorously while conc. ammonium hydroxide was added. After 1 h Z-3-amino-3-(2,4-dimethoxyphenyl)propanoic amide precipitated. The precipitate was isolated and washed with ether (2.1 g, 6.1 mmol, 91%).

A mixture of Z-3-amino-3-(2,4-dimethoxyphenyl)propanoic amide (0.7 g, 2.03 mmol) and 10% Pd/C (0.5 g) and 4.4% formic acid in water (20 ml) was stirred for 1 h at room temperature. The catalyst was removed by filtration and the clear solution was evaporated under reduced pressure whereby 3-amino-3-(2,4-dimethoxyphenyl)propanoic amide (0.43 g, 1.92 mmol, 94%) was isolated.

Mp: 148°–149° C., and the compound was identified by $^1$H-NMR spectroscopy.

B) Preparation of N-benzoyl-3-amino-3-(2,4-dimethoxyphenyl)propionic amide

Prepared analogously with N-benzoyl-2-nitrophenylglycine amide described in example 1B.

C) Solvolysis of N-benzoyl-3-amino-3-(2,4-dimethoxyphenyl)propionic amide

N-benzoyl-3-amino-3-(2,4-dimethoxyphenyl)propionic amide (6.09 mmol) was dissolved in TFA/thioanisole/pentamethylbenzene (2 ml/0.587 ml, 5 mmol/29.7 mg, 0.2 mmol). After 1 h the generated benzamide (4.99 mmol 82%) was determined quantitatively by HPLC using benzamide standard chromatograms.

EXAMPLE 11

Transacylation of Bz-Ala-OMe with 2,4-dimethoxybenzylamine as nucleophile using enzyme CPD-Y 2,4-dimethoxybenzylamine, HCl (41 mg) was added to 5 mM EDTA (2 ml, pH ~8.0), pH was adjusted to 9.5 with 5N NaOH, and Bz-Ala-OMe (20.1, 207 mg/ml MeOH) was added. A 0 sample was prepared by adding $CH_3CN$ (240 µl) to 10 µl reaction mixture. Subsequently CPD-Y (10 µl, 22 mg/ml $H_2O$) was added to the reaction mixture, and the reaction was followed by extracting and analyzing samples at 5, 30, 60 and 120 min. Each sample was analyzed using HPLC system-6 and the chromatograms compared to standard solutions of Bz-Ala-OMe and Bz-Ala-OH whereby the product distribution was determined, (the transacylation product yield was >60%). The reaction product was identified using mass spectrometry as Bz-Ala-2,4-dimethoxybenzylamide, $M_{wt}$=320.

The transacylation product may be transformed to Bz-Ala-$NH_2$ by solvolytic cleavage.

EXAMPLE 12

Preparation of N-protected Phe-$NH_2$ by transpeptidation and solvolytic cleavage A) Transpeptidation of Z-Phe-Ala-OH with 2,4-dimethoxybenzylamine using CPD-Y 2,4-Dimethoxybenzylamine, HCl (166 mg, 0.8 mmol) was added to 5 mM EDTA (2 ml, pH ~8.0), pH was adjusted to 8.5 with 5N NaOH, and Z-Phe-Ala-OH (10.1 of a solution of 68 mg/ml DMF) was added. A 0 sample was prepared by adding $CH_3CN$ (240 µl) to 10 µl reaction mixture. Subsequently CPD-Y (15 µl, 18 mg/ml $H_2O$) was added to the reaction mixture, and the reaction mixture was analyzed after 5, 60, 120 and 300 min. Each sample was analyzed using HPLC system-7 and the chromatograms compared to standard solutions of Z-Phe-Ala-OH and Z-Phe-OH, whereby the product distribution was determined; the transpeptidation product yield was ~60%. The reaction product was identified using mass spectrometry as Z-Phe-2,4-dimethoxybenzylamide, $M_{wt}$=448.5, and purified using HPLC system-7.

B) Solvolysis of Bz-Phe-2,4-dimethoxybenzylamide

Bz-Phe-2,4-dimethoxybenzylamide (4.2 mg) was dissolved in trifluoroacetic acid (1.0 ml) containing 10% (v/v) trifluoromethane sulfonic acid (TFMSA) and the reaction mixture was kept in the dark for 1 h at 20° C. TFA/TFMSA was removed by blowing with $N_2$ and the residue was suspended in 95% (v/v) $CH_3CN$ (1.0 ml). The reaction mixture was analyzed by HPLC system-7 and the generated Bz-Phe-$NH_2$ (>95%) was determined quantitatively using a Bz-Phe-$NH_2$ standard solution (Bz-Phe-$NH_2$ was purchased from Bachem, Switzerland).

EXAMPLE 13

Reductive cleavage of N-benzoylphenacylamine as model compound

Preparation of N-benzoylphenacylamine

Prepared as N-benzoyl-2-nitrophenylglycine amide described in example 1B.

Cleavage of N-benzoylphenacylamine

N-benzoylphenacylamine (10 mg, 41.8 mmol) was dissolved in 60% aqueous acetic acid (1 ml) and Zn-dust (20 mg) was added. Samples were taken every 15 min and N-benzoylphenacylamine, the generated benzamide and acetophenone were quantified by HPLC using standard samples of the respective compounds.

| Compound | 0 min | 15 min | 30 min |
|---|---|---|---|
| N-phenacylbenzamide | 100% | 17% | 0% |
| benzamide | 0% | 29% | 30% |
| acetophenone | 0% | 4% | 13% |

EXAMPLE 14

Rearrangement

A) Transacylation of Bz-Ala-OMe with allylamine using enzyme CPD-Y

EDTA (2 ml, 5 mM), pH ~8.0, was added to allylamine (11 mg). pH was adjusted to ~8.5 with 5N NaOH, and Bz-Ala-OMe (20 µl) of a solution of 207 mg/ml methanol (1M) was added. A 0 min sample was prepared by adding 200 µl methanol to 10 µl reaction mixture. Subsequently, CPD-Y (10 µl, 22 mg/ml $H_2O$ was added to the reaction mixture, and the reaction was followed by extracting samples at 10, 30 and 60 min. Each sample was analyzed using HPLC and the Bz-Ala-OH, whereby the product distribution was determined. The transacylation product may be transformed to Bz-Ala-$NH_2$ by rearrangement and hydrolysis.

B) Rearrangement and hydrolysis of N-benzoylallylamine (model compound) with LiOH N-Benzoylallylamine (161 mg, 1 mmol) was dissolved in 5 ml acetone and 5 ml 0.5N LiOH was added. The solution was stirred to 1 h at 20° C. Acetone was removed by blowing with $N_2$ and the aqueous solution, pH was adjusted to ~1.0 with 6N HCl. The reaction mixture was qualitatively analyzed by TLC to determine generated benzamide.

EXAMPLE 15

Preparation of Bz-Phe-NH$_2$ by oxidative cleavage

Oxidation of Bz-Phe-2,4-dimethoxybenzylamide

Bz-Phe-2,4-dimethoxybenzylamide prepared analogously with example 12 (8,4 mg) was dissolved in CH$_3$CN/H$_2$O (100:1) (2.0 ml). To this solution (NH$_4$)Ce(NO$_3$)$_6$(CAN) (15.4 mg) was added and the reaction mixture was kept in the dark for 2 h at 20° C. The reaction mixture was analyzed by HPLC system-7 and the generated Bz-Phe-NH$_2$ (>65%) was determined quantitatively using a Bz-Phe-NH$_2$ standard solution (Bz-Phe-NH$_2$ purchased from Bachem, Switzerland).

EXAMPLE 16

Preparation of Bz-Ala-Ala-Arg-2-nitrophenylglycine (SEQ ID NO:17) amide by transpeptidation A) Transpeptidation of Bz-Ala-Ala-Arg-Ala-Phe-Ala-OH (SEQ ID NO:18) with 2-nitrophenylglycine amide as nucleophile using trypsin To a solution of 400 mM 2-nitrophenylglycine amide and 2 mM CaCl$_2$ in DMF/H$_2$O (60/40 v/v, 120 µl pH ~6.5) was added 80 mM Bz-Ala-Ala-Arg-Ala-Phe-Ala-OH (SEQ ID NO:18) in DMF (3 µl). Trypsin (3 µl, 0.5 mg/ml in Hepes, 2 mM CaCl$_2$, pH 7.5) was added to the reaction mixture. The reaction was followed by extracting a sample at 93 min. The sample was analyzed using HPLC, and the chromatogram was compared with the chromatogram corresponding to the results from trypsin hydrolysis of Bz-Ala-Ala-Arg-Ala-Phe-Ala-OH and amino acid analysis of reaction products. The reaction mixture composition was as follows:

| | |
|---|---|
| Bz-Ala-Ala-Arg-Ala-Phe-Ala-OH (SEQ ID NO: 18): | 21% |
| Bz-Ala-Ala-Arg-OH (SEQ ID NO: 19): | 25% |
| Bz-Ala-Ala-Arg-2-nitrophenylgycine (SEQ ID NO: 17) amide: | 53% |

The fraction of aminolysis was ~68% and the product was purified by HPLC and identification was performed by determination of retention time, amino acid analysis and by mass spectrometry.

Same experiment performed with 800 mM 2-nitrophenylglycine amide and 1 µl trypsin (5 mg/ml).

The reaction mixture was analyzed after 55 min and composition was as follows:

| | |
|---|---|
| Bz-Ala-Ala-Arg-Ala-Phe-Ala-OH (SEQ ID NO: 18): | 11% |
| Bz-Ala-Ala-Arg-OH (SEQ ID NO: 19): | 19% |
| Bz-Ala-Ala-Arg-2-nitrophenylgycine (SEQ ID NO: 17) amide: | 70% |

The fraction of aminolysis was ~79% and the product was purified by HPLC and identification was performed by determination of retention time, amino acid analysis and by mass spectrometry.

REFERENCES:

1. Ajayaghosh, A. and Pillai, V. N. R. (1990), J. Org. Chem. 55, 2826–2829
2. Pillai, V. N. R., Mutter, M. and Bayer, F. (1979), Tetrahedron Letters 3409–3412
3. Pillai, V. N. R. and Mutter, M. (1980), J. Org. Chem. 45, 5364–5370
4. Rich, D. H. and Gurwara, S. K. (1975), Tetrahedron Letters 301–304
5. Wang, S.-S. (1976), J. Org. Chem., 41, 3258–3261
6. Penke B. and Rivier, J. (1987), J. Org. Chem., 52, 1197–1200
7. Widmer, F., Breddam, K. & Johansen, J. T. (1981), Carlsberg Res. Comm. 46, p. 97–106
14. Breddam, K., Widmer, F. & Johansen, J. T. (1980) Carlsberg Res. Commun. 45, 237–247
15. Breddam, K., Widmer, F. & Johansen, J. T. (1981) Carlsberg Res. Commun. 46, 121–128
16. Breddam, K., Johansen, J. T. & Ottesen, M. (1984) Carlsberg Res. Commun. 49, 457–462
17. Breddam, K. (1985) Carlsberg Res. Commun. 50, 309–323
18. Breddam, K. (1988) Carlsberg Res. Commun. 53, 309–320
21. Breddam, K. Sørensen, S. B. & Svendsen, I. (1987) Carlsberg Res. Commun. 52, 297–311
23. Breddam, K., Widmer, F. & Johansen, J. T. (1981) Carlsberg Res. Commun. 46, 361–372
25. Breddam, K. & Ottesen, M. (1984) Carlsberg Res. Commun. 49, 473–481
26. Breddam, K., Sørensen, S. B. & Ottesen, M. (1985) Carlsberg Res. Commun. 50. 199–209
28. Johansen, J. T., Breddam, K. & Ottesen, M. (1976) Carlsberg Res. Commun. 41. 1–14
30. Breddam, K., Sørensen, S. B. & Ottesen, M. (1983) Carlsberg Res. Commun. 48, 217–230
33. Kubota et al. Carboxypeptidase C$_N$ (1973), J. Biochem. 74, no. 4, 757–770

---

We claim:

1. A process for the preparation of a C-terminally amidated peptide, Peptide-NH$_2$, comprising:

reacting a substrate component with a nucleophile component in the presence of trypsin or a carboxypeptidase in a reaction medium to form a first reaction product Peptide-NH-R, wherein the reaction medium is an aqueous reaction medium or an organic solution at a pH sufficient to maintain the activity of said trypsin or carboxypeptidase; and cleaving the first reaction product, Peptide-NHR, by a non-enzymatic chemical cleavage to form the C-terminally amidated peptide, Peptide-NH$_2$;

the substrate component is selected from the group consisting of:

a) C-terminally unblocked peptides of the formula, Peptide-OH;

b) peptides or peptide derivatives of the formula, Peptide-X-Y, where X is an amino acid residue or a peptide residue and Y is any C-terminal modification compatible with the other steps of the method; and c) C-terminally esterified peptides of the formula, P-OR', where R' is alkyl, aryl, heteroaryl, aralkyl or an d-des amino fragment of an amino acid; and the nucleophile component is an amino group containing compound, NH$_2$-R, which is clearable so that the first reaction product, Peptide-NH-R, can be converted into Peptide-NH$_2$; the nucleophilic component, NH$_2$-R, being selected from the group consisting of:

a) a derivative with the general formula

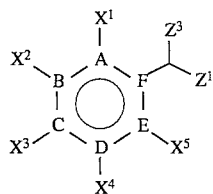

wherein A-F are carbon atoms or up to two of A-F are nitrogen atoms; $Z^3$ is H, straight chain or branched $C_1$–$C_6$ alkyl, aryl, aralkyl an oxo group, a carboxylic acid or salt thereof, a carboxylic acid ester, a nitrile, or a carboxylic acid amide which may be substituted on N with $C_1$–$C_6$ alkyl, aryl or aralkyl; $X^1$–$X^5$ independently are hydrogen, $C_1$–$C_3$ alkyl, halogen, cyano, methoxy, hydroxy, sulfo, amino or nitro, or any two of $X^1$–$X^5$ may join to form a fused aliphatic or aromatic ring and when any of A-E is nitrogen, the corresponding X is void or is oxygen; $Z^1$ is an amino or an amine derivative of the general formula

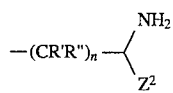

wherein $Z^2$ is as defined for $Z^3$ except for an oxo group, n is an integer from 0 to 5, and R' and R" are as defined for $Z^3$;

b) a derivative of the general formula

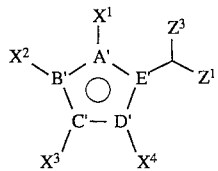

wherein A'-E' are carbon atoms, or one of A'-E' is an oxygen or sulphur atom or up to two of A'-E' are nitrogen atoms, $Z^1$, $Z^3$, and $X^1$–$X^4$ are as defined above, and when any of A'-E' are nitrogen, the corresponding X is void or is oxygen and when any of A'-E' is oxygen or sulphur, the corresponding X is void; and c) an allylamine compound with the general formula:

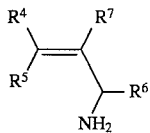

wherein $R^4$–$R^7$ are independently hydrogen, straight chain or branched $C_1$–$C_6$ alkyl, aryl, a carboxylic acid or salt thereof, a carboxylic acid ester, a nitrile, or a carboxylic acid amide which may be substituted on N with $C_1$–$C_6$ alkyl, aryl or aralkyl.

2. The process according to claim 1, comprising cleaving the first reaction product by photolysis.

3. The process according to claim 2, wherein the photolysis is performed on an aqueous solution of the peptide.

4. The process according to claim 3, wherein the photolysis is performed at a wave length of about 300–800 nm.

5. The process according to claim 3, wherein the aqueous solution includes an organic solvent.

6. The process according to claim 2, wherein the photolysis is performed on an organic solution of the first reaction product.

7. The process according to claim 6, wherein the organic solution includes a reducing agent.

8. The process according to claim 1, wherein said cleavage is performed by solvolysis.

9. The process according to claim 8, wherein the solvolysis is performed in an acid medium.

10. The process according to claim 9, wherein the solvolysis is performed in an acid medium selected from the group consisting of trifluoroacetic acid and aqueous trifluoroacetic acid.

11. The process according to claim 1, wherein said cleavage is performed by reduction.

12. The process according to claim 11, wherein the reduction is performed as a catalytic reduction.

13. The process according to claim 12, wherein the catalytic reduction is a catalytic hydrogenation.

14. The process according to claim 1 wherein the nucleophile component is an allylamine compound with the general formula:

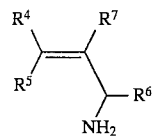

wherein $R^4$–$R^7$ are as defined in claim 1.

15. The process according to claim 1, comprising cleaving the first reaction product by rearrangement and hydrolysis or by elimination.

16. The process according to claim 1, comprising cleaving the first reaction product by oxidation.

17. The process according to claim 1, wherein the enzyme is a carboxypeptidase.

18. The process according to claim 17, wherein the carboxypeptidase is selected from the group consisting of carboxypeptidase Y from yeast, carboxypeptidase S-1 and S-22 from Penicillium janthinellum, carboxypeptidases from Aspergillus saitoi or Aspergillus oryzae, carboxypeptidases C from orange leaves or orange peels, carboxypeptidase $C_N$ from Citrus natsudaidai Hayata, phaseolain from bean leaves, carboxypeptidases M-I and M-II from germinating barley, carboxypeptidase W-II from wheat bran, and carboxypeptidases from germinating cotton plants, tomatoes, watermelons and Bromelein powder.

19. The process according to claim 1 wherein the reaction medium comprises an organic solvent.

20. The process according to claim 19, wherein the organic solvent is selected from the group consisting of alkanols, alkanoic acids, dimethylsulfoxide, dimethylformamide, dioxane, tetrahydrofuran, and dimethoxyethane.

21. The process according to claim 20 wherein the alkanols include glycerol, ethylene glycol or polyethylene glycol.

22. The process according to claim 1, wherein the enzyme is trypsin.

23. The process according to claim 1, wherein the aralkyl is $CH_2R^2$ or $CHR^2R^3$, and $R^2$ and $R^3$ are independently unsubstituted aryl groups or aryl groups substituted with halogen, hydroxy, alkoxy, nitro, amino or $C_1$–$C_6$ alkyl.

24. The process according to claim 1 wherein the nucleophile component is a derivative with the general formula:

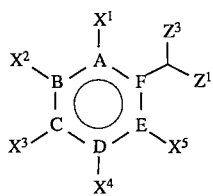

wherein A-F, $Z^1$, $Z^3$, and $X^1$–$X^5$ are as defined in claim 1.

25. The process according to claim 24, wherein the nucleophile component is a 2-nitroarylmethylamine derivative of the general formula:

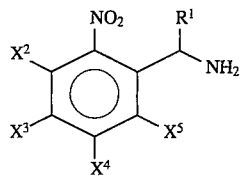

wherein $R^1$ represents H, straight chain or branched $C_1$–$C_6$ alkyl, aryl, aralkyl, a carboxylic acid or salt thereof, a carboxylic acid ester, a nitrile, or a carboxylic acid amide which may be substituted on N with $C_1$–$C_6$ alkyl, aryl, aralkyl; $X^2$–$X^5$ independently represent H, $C_1$–$C_3$ alkyl, halogen, cyano, methoxy, hydroxy, sulfo or nitro, or any two of $X^2$–$X^5$ may join to form a fused aliphatic or aromatic ring.

26. The process according to claim 1 wherein the nucleophile component $NH_2$-R is a benzylamine derivative of the formula:

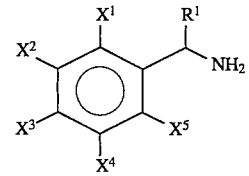

wherein $R^1$ is hydrogen, straight chain or branched $C_1$–$C_6$ alkyl, aryl, aralkyl, a carboxylic acid or a salt thereof, a carboxylic acid ester, a nitrile, or a carboxylic acid amide which may be substituted on N with $C_1$–$C_6$ alkyl, aryl or aralkyl; and $X^1$–$X^5$ independently are H, $C_1$–$C_3$ alkyl, halogen, hydroxy, $C_1$–$C_3$ alkoxy, nitro, sulfo, cyano or carboxy.

27. The process according to claim 1, wherein the Peptide is an N-protected peptide residue.

* * * * *

UNITED STATES PATENT AND TRADEMARK OFFICE
CERTIFICATE OF CORRECTION

PATENT NO. : 5,580,751

DATED : Dec. 3, 1996

INVENTOR(S) : Buchardt et al.

It is certified that error appears in the above-identified patent and that said Letters Patent is hereby corrected as shown below:

In column 5, line 41, "6" should read --5--; line 43, "5" should read --6--.

In column 13, line 35, "atkyl" should read --alkyl--.

In column 14, line 64, "Carboxpeptidase(s)C" should read --Carboxypeptidase(s)C--.

In column 16, line 56, delete "(SEQ ID NO: 11)" after the letters "NH$_2$"; line 57, insert --(SEQ ID NO: 11)-- after the letters "NH$_2$".

In column 19, line 36, "(10gl)" should read --(10µl)--; line 38, "10gl" should read --10µl--.

In column 20, line 65, insert --(SEQ ID NO: 14)-- after the letters "OH" (second occurrence).

Col. 21, line 2, "NO: 1)" should read --NO: 13)--.

In column 22, line 44 "NO: 15)" should read --NO: 10)--; line 52, "(4.1, 49 mg/ml" should read --(4µl, 49mg/ml--.

UNITED STATES PATENT AND TRADEMARK OFFICE
CERTIFICATE OF CORRECTION

PATENT NO. : 5,580,751

DATED : Dec. 3, 1996

INVENTOR(S) : Buchardt et al.

It is certified that error appears in the above-identified patent and that said Letters Patent is hereby corrected as shown below:

In column 25, line 32, "(20.1" should read --(20µl--; line 57, "(10.1" should read --(10µl--.

Signed and Sealed this

Twenty-fourth Day of March, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,580,751

DATED : December 3, 1996

INVENTOR(S) : Buchardt et al.

It is certified that error appears in the above-identified patent and that said Letters Patent is hereby corrected as shown below:

In col. 36, claim 1, line 25, change "clearable" to --cleavable--.

Signed and Sealed this

Sixteenth Day of June, 1998

Attest:

BRUCE LEHMAN

*Attesting Officer*     Commissioner of Patents and Trademarks

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 4 amino acids
        ( B ) TYPE: amino acid (C) STRANDEDNESS: single
(D) TOPOLOGY: linear (i i) MOLECULE TYPE: peptide (x i) SEQUENCE DESCRIPTION: SEQ ID NO:1:

Xaa Ala Ala Ala
1

(2) INFORMATION FOR SEQ ID NO:2:

(i) SEQUENCE CHARACTERISTICS:
(A) LENGTH: 4 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:2:

Xaa Ala Ala Leu
1

(2) INFORMATION FOR SEQ ID NO:3:

(i) SEQUENCE CHARACTERISTICS:
(A) LENGTH: 5 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:3:

Xaa Pro Lys Thr Thr
1               5

(2) INFORMATION FOR SEQ ID NO:4:

(i) SEQUENCE CHARACTERISTICS:
(A) LENGTH: 4 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:4:

Xaa Phe Phe Gly
1

(2) INFORMATION FOR SEQ ID NO:5:

(i) SEQUENCE CHARACTERISTICS:
(A) LENGTH: 4 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:5:

Xaa Pro Lys Ala
1

(2) INFORMATION FOR SEQ ID NO:6:

(i) SEQUENCE CHARACTERISTICS:
(A) LENGTH: 4 amino acids
(B) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:6:

Xaa Pro Lys Thr
1

( 2 ) INFORMATION FOR SEQ ID NO:7:

( i ) SEQUENCE CHARACTERISTICS:
( A ) LENGTH: 3 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:7:

Xaa Pro Thr
1

( 2 ) INFORMATION FOR SEQ ID NO:8:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:8:

Xaa Ala Pro Ala
1

( 2 ) INFORMATION FOR SEQ ID NO:9:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:9:

Tyr Gly Trp Met Asp Phe Ala
1               5

( 2 ) INFORMATION FOR SEQ ID NO:10:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:10:

Pro Gln Thr Ala Ile Gly Val Gly Ala Pro Ala
1               5                   1 0

( 2 ) INFORMATION FOR SEQ ID NO:11:

( i ) SEQUENCE CHARACTERISTICS:
( A ) LENGTH: 6 amino acids
( B ) TYPE: amino acid (C) STRANDEDNESS: single
(D) TOPOLOGY: linear (ii) MOLECULE TYPE: peptide (xi) SEQUENCE DESCRIPTION: SEQ ID NO:11:

Tyr Gly Trp Met Asp Xaa
1               5

(2) INFORMATION FOR SEQ ID NO:12:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:12:

Pro Gln Thr Ala Ile Gly Val Gly Ala Xaa
1               5                   10

(2) INFORMATION FOR SEQ ID NO:13:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:13:

Xaa Ala Pro Xaa
1

(2) INFORMATION FOR SEQ ID NO:14:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:14:

Xaa Ala Pro Ala
1

(2) INFORMATION FOR SEQ ID NO:15:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:15:

Tyr Gly Trp Met Asp Phe Xaa
1               5

(2) INFORMATION FOR SEQ ID NO:16:

(i) SEQUENCE CHARACTERISTICS:
    (A) LENGTH: 11 amino acids
    (B) TYPE: amino acid (C) STRANDEDNESS: single
(D) TOPOLOGY: linear (ii) MOLECULE TYPE: peptide (xi) SEQUENCE DESCRIPTION: SEQ ID NO:16:

Pro Gln Thr Ala Ile Gly Val Gly Ala Pro Xaa
1               5                   10

(2) INFORMATION FOR SEQ ID NO:17:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:17:

Xaa Ala Arg Xaa
1

(2) INFORMATION FOR SEQ ID NO:18:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:18:

Xaa Ala Arg Ala Phe Ala
1               5

(2) INFORMATION FOR SEQ ID NO:19:

(i) SEQUENCE CHARACTERISTICS:
(A) LENGTH: 3 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:19:

Xaa Ala Arg
1